United States Patent [19]
Ziege et al.

[11] Patent Number: 5,100,805
[45] Date of Patent: Mar. 31, 1992

[54] QUANTITATIVE IMMUNOASSAY SYSTEM AND METHOD FOR AGGLUTINATION ASSAYS

[75] Inventors: Garth E. Ziege, Sheridan; Patricia C. Andrews, Camby; Andris Indriksons, Zionsville; Lawrence E. Kay, Greenwood; Jeffrey E. Wright; Daniel A. Maude, both of Indianapolis, all of Ind.

[73] Assignee: Seradyn, Inc., Indianapolis, Ind.

[21] Appl. No.: 301,969

[22] Filed: Jan. 26, 1989

[51] Int. Cl.$^5$ .......................................... G01N 33/557
[52] U.S. Cl. ........................................ 436/517; 422/57; 422/61; 422/62; 422/63; 422/67; 422/73; 422/82.05; 436/531; 436/533; 436/534; 436/805; 436/807
[58] Field of Search ............... 436/517, 528, 531, 533, 436/534, 805, 807; 422/57, 61, 62, 68, 63, 67, 73

[56] References Cited

U.S. PATENT DOCUMENTS

| | | | |
|---|---|---|---|
| 2,666,355 | 1/1954 | Trurnit | 88/14 |
| 3,310,680 | 3/1967 | Hasegawa | 250/218 |
| 3,653,767 | 4/1972 | Liskowitz | 356/102 |
| 3,705,721 | 12/1972 | Friedman | 356/30 |
| 3,758,787 | 9/1978 | Sigrist | 250/574 |
| 3,824,402 | 7/1974 | Mullaney | 250/565 |
| 3,905,767 | 9/1975 | Morris | 23/230 |
| 3,942,897 | 3/1976 | Takahashi et al. | 356/197 |
| 3,967,901 | 7/1976 | Rodriguez | 356/103 |
| 3,984,533 | 10/1976 | Uzgiris | 424/12 |
| 3,990,851 | 11/1976 | Gross | 23/253 |
| 4,011,044 | 3/1977 | Uzgiris | 23/230 |
| 4,080,264 | 3/1978 | Cohen et al. | 195/103.5 A |
| 4,118,192 | 10/1978 | Sawai et al. | 424/12 |
| 4,164,558 | 8/1979 | von Schulthess | 424/12 |
| 4,174,952 | 11/1979 | Cannell et al. | 23/230 |
| 4,203,724 | 5/1980 | Sawai et al. | 23/230 B |
| 4,208,185 | 6/1980 | Sawai et al. | 23/230 B |
| 4,264,766 | 4/1981 | Fischer | 536/31 |
| 4,521,521 | 6/1985 | Abbott et al. | 436/517 |
| 4,536,478 | 8/1985 | Sokoloff et al. | 436/533 |
| 4,563,431 | 1/1986 | Pauly et al. | 436/533 |
| 4,721,681 | 1/1988 | Lentrichia et al. | 436/523 |
| 4,766,083 | 8/1988 | Miyashita et al. | 436/517 |

OTHER PUBLICATIONS

Blume, Philip and Greenberg, Leonard J., "Application of Differential Light Scattering to the Latex Agglutination Assay for Rheumatoid Factor", *Clinical Chemistry*, vol. 21, No. 9, (1975), pp. 1234–1237.

Oreskes, Irwin and Singer, Jacques M., "The mechanism of Particulate Carrier Reactions", *Journal of Immunology*, vol. 86, (1961), 338–343.

Tengerdy, Robert P. and Small, William H., "Reaction Kinetic Studies of the Antigen–Antibody Reaction", *Nature*, May 14, 1966, pp. 708–710.

*Primary Examiner*—Christine Nucker

[57] ABSTRACT

An improved, copolymer-based immunoassay system, method, and apparatus is highly sensitive and effective in accurately measuring extremely low concentrations, such as $10^{-6}$ to $10^{-12}$ grams per milliliter, of biologically active substances, such as monoclonal or polyclonal antibodies and antigens, cancer markers, proteins, bacteria, viruses, therapeutic drugs, drugs of abuse, and food and water contaminants in fluid samples. The system requires no sample preparation, and is reliable, easy to use, sufficiently low in cost to be readily usable in doctors' offices, small labs, and other low-volume facilities, but is also readily adaptable to hospital and high-volume use. The new system, method, and apparatus for agglutination immunoassay systems includes novel and coordinated carrier particle technology, light application and measurement and chemistry, coacting to provide the multiple advantages of simplicity and accuracy in use, and extreme sensitivity in application, in quantifying immunoassays.

55 Claims, 9 Drawing Sheets

QUANTITATIVE IMMUNOASSAY SYSTEM AND METHOD FOR AGGLUTINATION ASSAYS

BACKGROUND OF THE INVENTION

The present invention relates generally to a system, method, and apparatus for determining the concentration of a substance of interest in a fluid sample. More particularly, the invention relates to a copolymer-based immunoassay system and method and apparatus coacting to quantitatively measure the concentration of biologically active substances capable of promoting or inhibiting agglutination reactions.

The medical community has a continuing need for improved procedures for measuring the concentration of biologically active substances, e.g., antigens and antibodies, in body fluids. Such procedures are needed, for example, to measure the concentration of drugs, hormones, and other substances in blood, serum, plasma, urine, and other body fluids as an aid in medical diagnosis and in the administration of drugs.

Various immunoassay procedures have been developed to determine the presence of biologically active substances in fluid samples. Perhaps the dominant immunoassay approach in use today is radioimmunoassay (RIA). In this method, a sample containing an unknown concentration of antigen is mixed with a fixed amount of antibody and a fixed amount of antigen which has been radioactively labelled. The resultant antibodyantigen complex is recovered and its radioactivity measured to determine the relative concentrations of the radioactive antigen and the antigen contributed by the sample to determine the concentration of the antigen in the sample.

Radioimmunoassay is popular because of its relatively high sensitivity. It suffers, however, from many well-known limitations including a relatively short shelf life, the necessity of handling radioactive materials, and the disposal problems associated with such materials. Also, radioimmunoassay systems are relatively expensive and, thus, are generally used only in large clinics and hospitals where there is sufficient testing volume to make the equipment cost effective. Radioimmunoassay methods are also generally not used for measuring antibody concentrations and are usually used in applications in which antigen concentrations are to be measured.

Enzyme immunoassay has replaced radioimmunoassay in some segments of the market; and although enzyme immunoassay is gaining in popularity, the sensitivity of this technique is still limited. In addition, the sophistication of the instrumentation and the resultant high skill level required of the technician would also appear to limit this procedure to hospitals and other large facilities.

Agglutination immunoassays have been in use for over thirty years. The agglutination reaction involves the in vitro aggregation of microscopic carrier particles as a result of the specific reaction between antibodies and antigens, one of which is immobilized on the surface of carrier particles. Early systems used red blood cells as carrier particles, while more recent systems also utilize latex-based particles.

Agglutination immunoassays are performed in two basic formats, direct and indirect. In the direct format, carrier particles are sensitized by attaching a specific antibody to the surfaces of the carrier particles. A fluid test sample is then mixed with a suspension of the sensitized carrier particles, and if the corresponding antigen is present in the test sample, the particles agglutinate through the resulting antibody-antigen binding reaction. By detecting the agglutination reaction, the presence of the antigen in the test sample can be confirmed.

Alternatively, an antigen can be attached to the surfaces of the carrier particles to detect the presence of the corresponding antibody in the test sample.

In the indirect format, to the extent to which a quantity of antibody (or antigen) of interest is present in a test sample, the antibody (or antigen) of interest inhibits the aggregation of the carrier particles that would otherwise have occurred; and the degree of inhibition indicates the concentration of the antigen (or antibody) of interest in the test sample.

The agglutination test is typically performed on a slide and read visually, and is a highly subjective test requiring substantial expertise. When no agglutination occurs, the mixture appears homogeneous and milky (when latex particles are used as the carrier particles); whereas, when aggregation occurs, the latex particles initially appear granular and, with time, become clumped. Because of the generally subjective nature of interpreting the results of the reaction, it is difficult to extract quantitative information, making the process unsatisfactory in many applications, for example, to monitor hormone levels or to detect cancer markers.

Because of the highly qualitative and subjective nature of prior agglutination immunoassay systems, various efforts have been directed toward developing systems capable of providing a more quantitative measurement. In addition, it has long been a desideratum to provide very sensitive immunoassay systems that are not dependent on large expensive apparatus and complicated and sensitive sample preparation procedures.

In U.S. Pat. No. 4,721,681 to Lentrichia et al., for example, an agglutination immunoassay system is described in which a sample containing, for example, an antigen of interest is reacted with a first reagent containing antibody-coated, light particles and a second reagent containing antigen-coated, heavy particles in a centrifugal field. Differential migration of first particles, second particles, and first particles linked to second particles by an agglutination reaction leaves a concentration of particles in suspension at a locus over time, which concentration is a function of the concentration of the antigen of interest in the test sample.

U.S. Pat. No. 4,264,766 to Ernst A. Fischer describes a latex polymer and process for its manufacture to provide improved latex particles for agglutination immunoassay tests. In the Fischer patent, latex carrier particles with a size range of about 0.01 microns to about 0.9 microns and a specific gravity of about 1.0 are provided with a covalently bound, water-soluble polyhydroxy compound capable of covalently binding an immuno active agent. The latex particles are manufactured in an aqueous latex suspension by reacting the suspended latex particle, having reactive functional groups selected from a group consisting of carboxyl, amino, amido or nitrile groups, with a water-soluble polyhydroxy compound.

U.S. Pat. Nos. 4,118,192; 4,203,724; and 4,208,185 to Sawai et al. describe an agglutination immunoassay system in which antibody- or antigen-sensitized latex particles, with an average diameter not greater than 1.6 microns, are irradiated with light (substantially monochromatic or polychromatic) having a wavelength in the range of 0.6 to 2.4 microns and longer than the average diameter of the carrier particles by a factor of at least 1.5, and the absorbance of the reaction mixture is measured as the reaction takes place. The described system uses insoluble carrier particles such as lattices of organic polymers such as polystyrene and styrene butadiene copolymer, dispersed coccal bacteria as well as microparticles of inorganic oxides and finely pulverized minerals, metals, and the like. Light sources may include tungsten lamps (monochromatically filtered or unfiltered), xenon lamps, halogen lamps, the Nernst glower, nichrome wire, or light-emitting diodes, with Ga-As light-emitting diodes being particularly favored. Light is split and transmitted through the reaction product and through a control sample for compensation purposes and is measured by two photocells such as those having lead sulfide, photoconductive elements. The photocell's outputs were amplified and recorded with time to provide data. Such systems have been incorporated by Mitsubishi Chemical Industries Limited into large hospital immunoassay facilities, but have failed to provide sensitivities in the range of $10^{-6}$ grams/milliliter to $10^{-12}$ grams/milliliter.

U.S. Pat. No. 4,080,264 to Cohen et al. discloses an agglutination immunoassay procedure which utilizes light-scattering spectroscopy to determine the concentration of an antibody or antigen of interest in a test sample. In Cohen et al., the mean diffusion constant of the agglutination reaction product is examined by quasi-elastic light-scattering spectroscopy and compared with predetermined mean diffusion constants to provide a quantitative measure of the concentration of the antibody or antigen of interest in the test sample. In Cohen et al., the light source is a laser. Such components are relatively expensive to purchase and maintain, provide errant outputs, and render the system useful in only relatively high-volume facilities. Such systems have been shown to have a substantial lack of sensitivity and are unable to accurately detect an agglutination reaction unless a high degree of agglutination has taken place, i.e., there is a substantially high concentration of the substance of interest.

U.S. Pat. No. 4,174,952 of Cannell et al. describes an agglutination immunoassay system in which the ratio of the intensity of light scattered at two different angles is measured and compared with standard measurements of known concentrations. This system has also been shown to have an unsatisfactory sensitivity and is too expensive for use in private physicians' offices or small labs.

SUMMARY OF THE INVENTION

The present invention is an improved, copolymer-based immunoassay system, method, and apparatus which is highly sensitive and effective in accurately measuring extremely low concentrations, such as $10^{-6}$ to $10^{-12}$ grams per milliliter, of biologically active substances, such as monoclonal or polyclonal antibodies and antigens, cancer markers, proteins, bacteria, viruses, therapeutic drugs, drugs of abuse, and food and water contaminants in fluid samples, requires no sample preparation for aqueous samples, and is reliable, easy to use, sufficiently low in cost to be readily usable in doctors' offices, small labs, and other low-volume facilities, but is also readily adaptable to hospital and high-volume use.

The invention comprises a new method, apparatus, and system for agglutination immunoassay systems including novel and coordinated carrier particle technology, light application and measurement, and chemistry, coacting to provide the multiple advantages of simplicity and accuracy in use and extreme sensitivity in application in quantifying immunoassays.

In the invention, novel reagent compositions permit the detection and measurement of extremely low concentrations of antibodies or antigens in a test sample in a simple and highly effective manner. The novel reagent compositions include new copolymer-based particles which are extremely uniform in size (e.g., 0.18 microns ±0.01 microns) such that the particles are all within a very narrow size distribution (i.e., C.V. = ±2%). In addition, the new copolymer particles comprise a new composition which does not readily interact non-specifically with body fluids and which coacts with the new light application and measurement system, i.e., the new particles may be relied upon to agglutinate in response to specific biologically active substances when so prepared and are capable of scattering light effectively. Also, the particles have been treated to ensure that sufficient quantities of antigens or antibodies can be irreversibly attached to their surfaces to cause their immuno-reactivity and to ensure that nonspecific agglutination reactions do not occur while the specific agglutination reaction intended is not unduly inhibited. Use of the new copolymer particles and their coaction with light in the system of this invention permit detection of an agglutination reaction at the earliest stages of a reaction and at extremely low concentrations of biologically active substances. The system of the invention can thus comprise a reagent including a buffered suspension of the new, uniformly sized, polymeric particles adapted to resist non-specific reaction to body fluids and to provide good light-scattering properties, sensitized by the attachment of functional groups onto their surfaces to allow for the covalent attachment of antigens, or antibodies, or other biologically active substances thereto in an agglutination reaction.

The system further includes a new means for illuminating such an agglutination reaction through a transparent container with high-intensity light and for detecting light scattered by such polymeric particles during the agglutination reaction. A detector detects light scattered by the mixture in a forward direction at an acute angle within a range from about 10° to about 20° relative to the path of the illuminating light and generates output signals proportional to the intensity of the detected scattered light. The system further includes means to digitize the output signal of the detector; memory means for receiving and storing digital data representing the intensity of the detected scattered light at a specified time, or times, during a test, for storing standard curve data representing the concentration of a substance of interest as a function of detected light intensity at a specified time, or times, during a test and for storing a system-operating program; means for comparing the stored test data in the memory means with the standard curve data in the memory means; and output means coupled to said comparing means for providing a quantitative measure of the concentration of the substance of interest in the fluid sample. The system of the invention can also store and compare the rate of change of such test data and standard curve data at various times during a test.

In a presently preferred embodiment of the invention, the new light application and measurement system comprises a controlled intensity, light-emitting diode producing light at a wavelength of about 660 nanometers, a collimator and aperture system, and a detector comprising a photodiode, such as a silicon photodiode. The use of the new light application and measurement system, rather than lasers and photomultiplier tubes or photocells as in prior systems, results in a system that is "errant free" (i.e., free of unwanted, immaterial output variation) and more sensitive in light-scattering immunoassay systems and that is of reduced size and cost and of greater reliability. The system provides a novel arrangement of aperture plates positioned between the light source and the transparent container and provided with apertures to coact with the collimated light to provide consistent and accurate detection of the light scattered by the reaction. In addition, in the new preferred system, suitable software is provided to maintain the intensity of the light at a constant level, and the gain of the signal from the detector may be varied, as explained below, for different tests.

In a presently preferred embodiment, the processing and controlling system comprises memory means including a first random access memory for increased flexibility in permitting the system to be used to perform different tests, a second electrically programmable memory for the operating system, and a third replaceable memory means to permit the system to store varied test procedures and data for biologically active substances of interest and to be updated for new and improved test procedures; and the comparing means comprises a micro-controller for calculating the concentration of the substance of interest in the test sample, for calibrating the system and, generally, for monitoring and controlling the operation of the system.

The immunoassay method of the invention comprises the steps of preparing the uniformly sized particles formed of polymeric materials selected to enhance their resistance to non-specific reaction with body fluids and their light-scattering properties; sensitizing the particles by providing at their surfaces functional groups adapted to bind an antibody or antigen for testing the biologically active substance of interest; and attaching to the functional groups either an antibody or an antigen for testing for the biologically active substance of interest.

Further steps depend upon the biologically active substance of interest in the test and whether the test is conducted in a direct or an indirect format. For example, where the method of the invention tests for Theophylline, a widely prescribed bronchial dialator (antiasthma drug), the preferred format is indirect and the method preferably includes the steps of providing a reagent solution comprising at least a buffer and an anti-Theophylline antibody; providing a reagent suspension comprising a buffered suspension of the sensitized uniformly sized copolymer particles with attached Theophylline antigen, preferably Theophylline-8-hydroxypropylamine; mixing the reagent solution with a serum test sample; mixing the reagent suspension with the mixture of the first reagent solution and the test sample; passing the high-intensity column of light through the mixture of test sample, reagent solution, and reagent suspension; measuring the intensity of the light scattered by the mixture at an acute angle to the light column as a function of time; storing data on the scattered light intensity as a function of time; and comparing the stored data with test data to determine the concentration of the substance of interest in the fluid sample.

The numerous other new tests now possible with the system and method of the present invention also include those for thyroxine ($T_4$), the most predominant thyroid hormone; triiodothyronine ($T_3$), the biologically most active thyroid hormone; thyrotopin, thyroid-stimulating hormone (TSH) which regulates thyroid gland function; and digoxin, a widely prescribed cardiac antiarrythmia drug. The system and method of the invention, because of its greater sensitivity, can include simple immunoassay tests for the above biologically active substances and others, for example, HCG, LH, ferritin, phenobarbitol, and phenytoin, and for cancer markers, proteins, bacteria, viruses, therapeutic drugs, drugs of abuse, and food and water contaminants.

In practicing the method of the invention, each substance to be measured uses a reagent composition specifically formulated to maximize the sensitivity of the test being performed. The various reagent compositions are initially mixed with standard quantities of the various biologically active substances of interest and examined by the system of the invention to develop, for each of the substances of interest, standard curve data representing the concentration of the substances of interest, e.g., data representing the reaction rate at a specified time, or times, data representing the rate of change of the reaction at any time, or times, or a combination thereof. The data representing these standard curves are entered into and stored in the memory means and compared with intensity test data generated by monitoring an agglutination reaction using an unknown test sample. The memory means stores the program of system calibration and sample analysis, and the system provides an output representing the concentration of the substance of interest in the unknown test sample.

In general, the present invention provides a highly sensitive system, method, and apparatus which is effective in reliably providing an accurate quantitative measurement of the concentration of biologically active substances, such as antibodies or antigens, in fluid samples down to the range of $10^{-6}$ to $10^{-12}$ grams per milliliter at relatively low cost. The present invention provides sensitivities of from 1,000 to 1,000,000 times greater than even large hospital-size agglutination testing systems currently in use. That is, the present invention permits rapid and accurate measurement of concentrations from 0.001 to 0.000001 times less than other currently used systems.

Further advantages and specific details of the invention will become apparent in conjunction with the following detailed description of a presently preferred embodiment.

BRIEF DESCRIPTION OF THE DRAWINGS

FIGS. 9, 10, and 11 are standard curve data used to calculate unknown concentrations of Theophylline in a serum or a body fluid.

DETAILED DESCRIPTION OF THE PREFERRED EMBODIMENT

The present invention is a new immunoassay system, method, and apparatus for quantitatively measuring the concentration of a biologically active substance, such as an antigen or an antibody, in a body fluid such as blood, serum, urine, or plasma by initiating an agglutination reaction in a mixture comprising a fluid sample and a reagent, and by measuring the extent of the agglutination reaction over time. In order to provide a clearer understanding of the present invention, it is useful to briefly explain the nature of the agglutination reaction and the manner in which the physical effect of the agglutination reaction provides information indicative of the concentration of a substance of interest.

Figure 1:
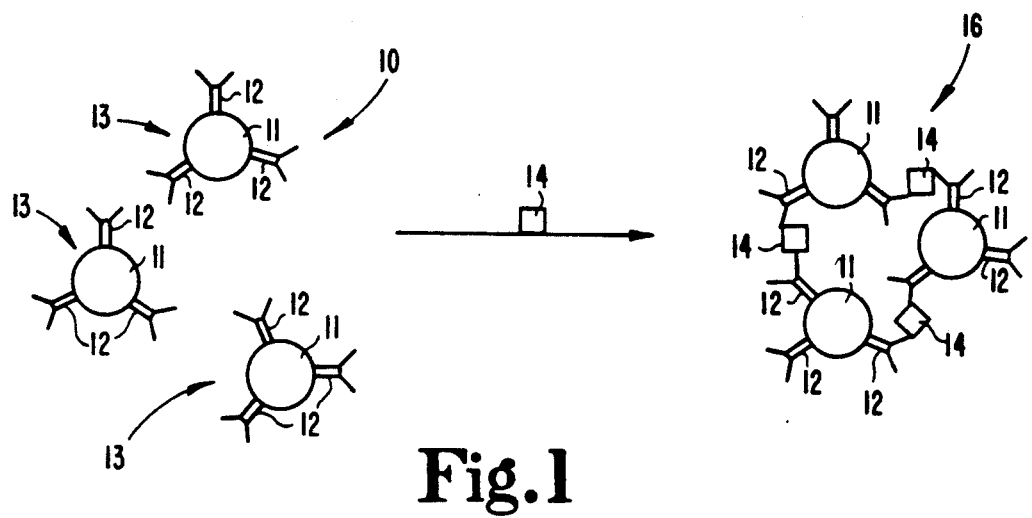
FIGS. 1 and 2 schematically illustrate direct formats of an agglutination reaction to help provide a clearer understanding of the invention.
Figure 2:
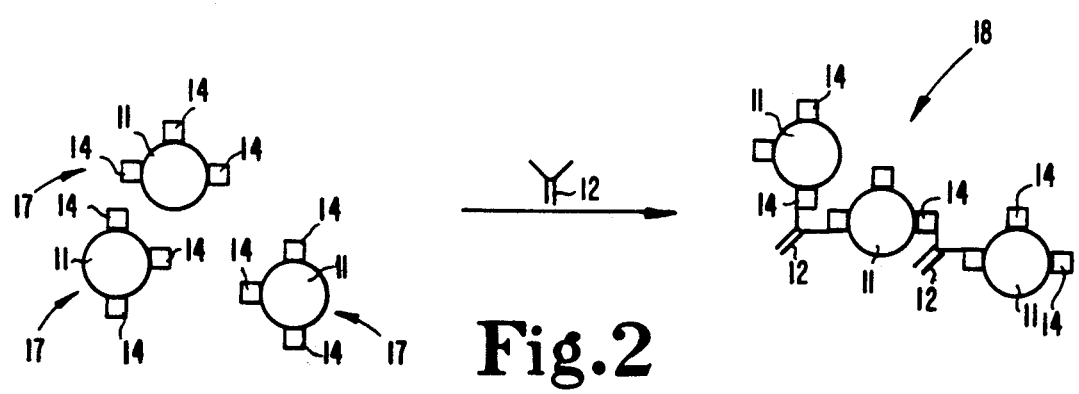

As indicated previously, an agglutination reaction can be run in two basic formats, direct or indirect. Direct formats are illustrated in FIGS. 1 and 2. In FIG. 1, a reagent suspension 10 contains a large number of carrier particles 11 which have been sensitized by the attachment of antibodies 12 to their surfaces to provide sensitized particles 13. The reagent suspension is then mixed with a fluid sample. If the fluid sample contains an antigen 14 which corresponds to antibody 12, sensitized particles 13 will agglutinate through the antibody-antigen binding reaction as illustrated at 16. Alternatively, as shown in FIG. 2, carrier particles 11 may be sensitized by the attachment of antigens 14 to their surface to provide sensitized particles 17. The reagent suspension is then mixed with a fluid sample; and if the sample contains corresponding antibodies 12, sensitized particles 17 will agglutinate as shown at 18.

In either of the direct formats illustrated in FIGS. 1 and 2, the degree of agglutination is a measure of the concentration of antigen 14 (FIG. 1) or antibody 12 (FIG. 2) in the fluid sample.

Figure 3:
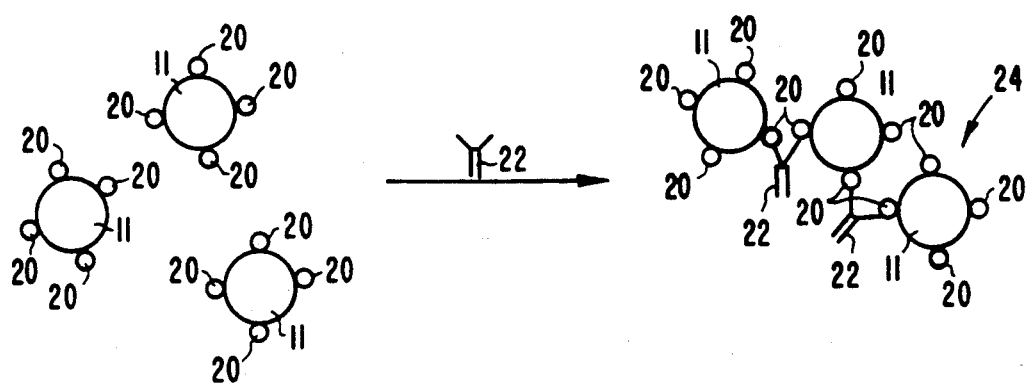
FIGS. 3 and 4 schematically illustrate an agglutination reaction in an indirect format to help provide a clearer understanding of the invention.
Figure 4:
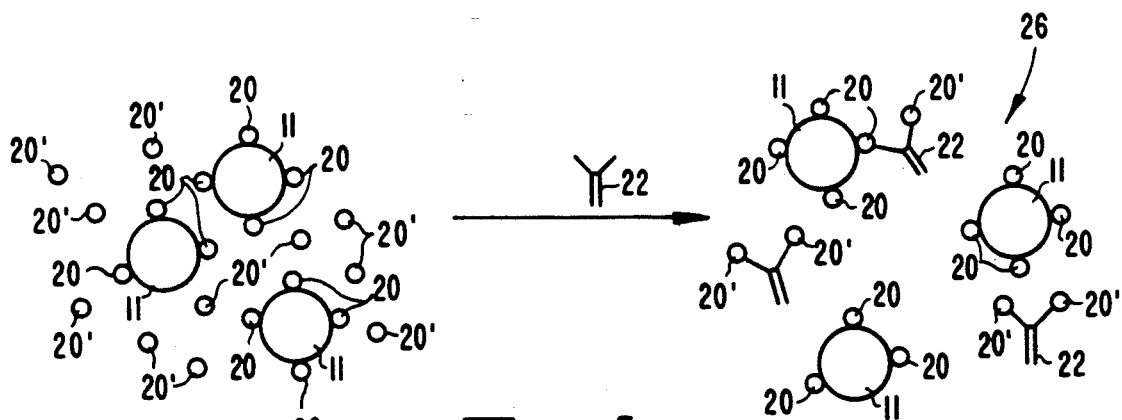

Indirect formats are illustrated in FIGS. 3 and 4, and for convenience are described with reference to one particular test that may also be carried out with the system of the present invention. In particular, within days of conception, the hormone human chorionic gonadotropin (HCG) will appear in the urine of a pregnant woman; and its level increases several hundredfold through the first trimester of pregnancy. The presence of this hormone in the urine is a clear indication of pregnancy and can readily be detected by using the indirect format of an agglutination reaction. In FIG. 4, HCG 20 affixed to the surface of latex particles 11 competes with any, HCG 20' present in the urine to react with an antibody 22 provided as a second reagent. When no HCG 20' is present in the urine, as shown in FIG. 3, antibody 22 is able to react with the HCG 20 on particles 11 to cause the agglutination reaction illustrated at 24. On the other hand, if HCG 20' is present in the urine, as shown in FIG. 4, the HCG 20' in the urine competes with the HCG 20 on particles 11 to significantly limit the amount of the agglutination of the sensitized particles as indicated at 26. In the indirect format, therefore, the greater the extent of agglutination, the lesser the concentration of the substance of interest in the fluid sample.

As indicated previously, the agglutination test was traditionally performed on a slide; and the degree of agglutination was read visually by a technician. In the specific indirect format test for the detection of HCG, with a positive test (HCG present), substantially no agglutination occurs; and the latex suspension appears homogenous and milky. With a negative test (HCG not present), substantial aggregation of sensitized latex particles occurs and provides the suspension with a granular appearance which, with time, becomes grossly clumped.

Because of the subjective nature of reading the results of the agglutination test, it was difficult to extract a high degree of quantitation from the appearance of the latex aggregates. The result is basically a qualitative one providing only a "yes" or "no" answer to the question of whether a particular substance is present in the sample. While such tests are satisfactory for use in pregnancy tests, they are not satisfactory for quantifying the presence of many antibodies and antigens of interest.

The present invention provides a system, method, and apparatus for quantitatively measuring, to a high degree of accuracy, and with a high degree of sensitivity, the extent of agglutination which occurs in an agglutination reaction and for automatically converting such information into data representing the concentration of a biologically active substance of interest.

Figure 5:
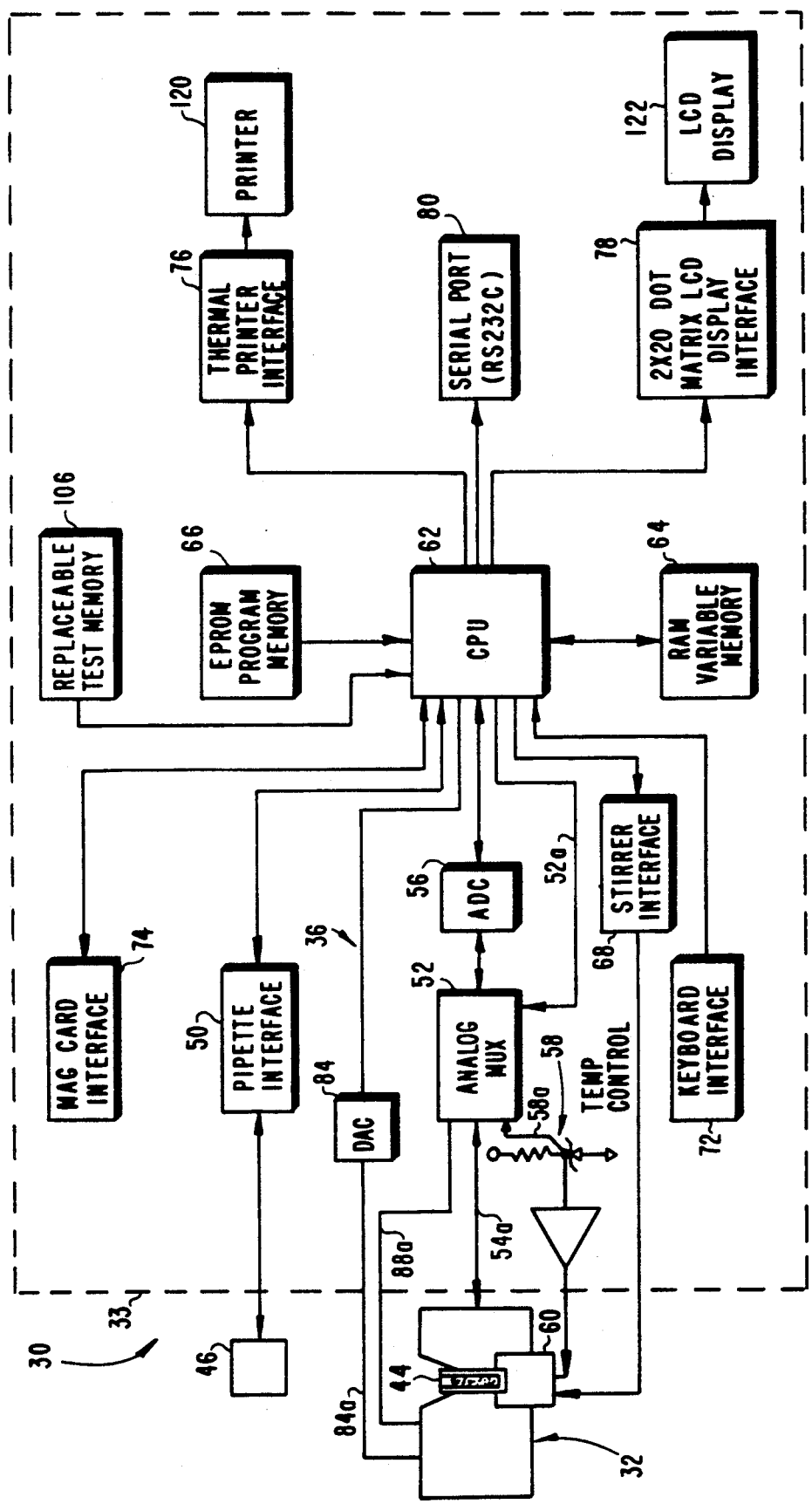
FIG. 5 illustrates the instrument schematic of the immunoassay system of a presently preferred embodiment of the invention for quantitatively measuring the concentration of biologically active substances capable of promoting or inhibiting an agglutination reaction.

FIG. 5 illustrates the instrument schematic of the agglutination immunoassay system according to a presently preferred embodiment of the invention. The system is generally designated by reference numeral 30 and include an errant-free light application and measurement system 32 for illuminating a fluid mixture comprised of a reagent suspension and a fluid sample in a transparent container 44 and for detecting and generating signals proportional to the degree of agglutination in the fluid mixture, and a controlling and processing system 33 for monitoring and controlling the operation of the light application and measurement system, for receiving data from the light application and measurement system, and for processing the received data to provide a quantitative measure of the concentration of a substance of interest in the fluid sample. In the preferred systems of the invention, the controlling and processing system also monitors and controls the light application and measurement system.

Figure 6:
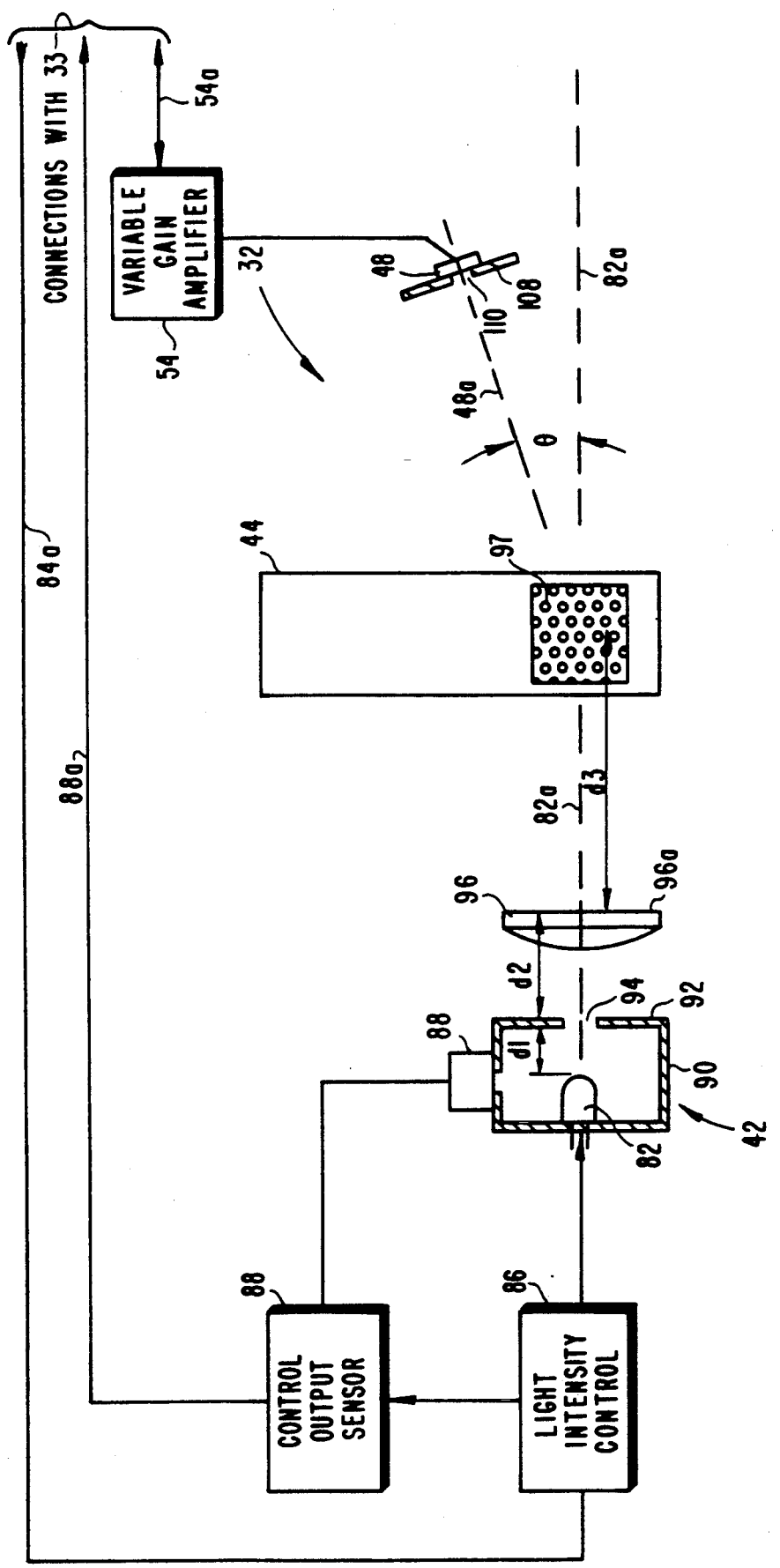
FIG. 6 schematically illustrates the light application and measurement system of FIG. 5 in greater detail.

Light application and measurement system 32 is illustrated in greater detail in FIG. 6. Generally, the light application and measurement system includes an illuminating means 42 for illuminating a mixture 97 of a reagent and a fluid sample in container 44, a collimator 96, and a detector 48 for detecting light scattered by the mixture in a forward direction at a selected acute angle 8 relative to the axis of illuminating light and for generating errant-free signals indicative of the intensity of the scattered light received by detector 48.

In the novel light application and measurement system, illuminating means 42 comprises a source 82 for producing light at high intensity. Light source 82 is preferably supported in a box 90 with an aperture plate 92 forming an aperture 94 with a diameter of 0.200 inch for the emission of light. The light emitted from aperture plate 92 is collimated by a lens 96 and directed through reagent/test-sample mixture 97 in transparent container 44 such as a round test tube, preferably a plastic cuvette having substantially parallel sides, such as a square test tube. Light source 82 comprises a light-emitting diode, such as a Stanley #H2000 or #H3000 LED capable of generating light having a wavelength of approximately 660 nanometers (red light) at a controllable intensity. The distance $d_1$ between the LED light source 82 and aperture plate 92 is 1.320 inches; the distance $d_2$ between aperture plate 92 and a light-emitting surface 96a of collimating lens 96 is 0.790 inch; and the distance $d_3$ between light-emitting surface 96a of the collimating lens and the center of cuvette 44 is 1.459 inches. The light used in the light application and measurement system is not polarized and is not filtered to provide monochromatic light. Light source 82 is coupled to a controlled, current source (not shown) which is included in a light intensity control 86.

In the preferred system of this invention, light intensity control 86 is connected with a microcontroller 62 (FIG. 5) of the controlling and processing system 33 through a digital-to-analog converter 84 and connection 84a. During setup and calibration of the system, light from light source 82 is projected through a cuvette with a suspension of particles that provides a known and constant scattering of light; and the resulting scattered light intensity is sensed and compared with standard data stored in the system memory, and any deviation of light intensity from standard can be corrected by operation of the light intensity control by microcontroller 62 through interconnected digital-to-analog signal converter 84. Upon determining that a correction of the intensity of light source 82 is needed, the microcontroller generates a digital signal to correct the intensity. The digital signal is converted to an analog signal by digital-to-analog converter 84, and the analog signal is applied over connection 84a to light intensity control 86 which increases or decreases the current through light source 82 to correct its intensity. A control output sensor 88 provides microcontroller 62 with an indication of the output of light intensity control 86 (i.e., the current through light source 82) over connection 88a and through an analog multiplexer 52 and an analog-to-digital converter 56. Microcontroller 62 can use such information to diagnose malfunctions of the system and their source. Microcontroller 62 is provided with instructions for such procedures in the instrument diagnostic test portion of the software.

In another embodiment of the system, light intensity control 86 can be connected directly with a light intensity detector (not shown) that is positioned in the light application and measurement system to receive light from light source 82 (e.g., through an additional opening in box 90); and the light intensity control 86 can use the output of the intensity detector to automatically maintain the intensity of the light at a substantially constant level that is established when the system is originally calibrated.

In the light application and measurement system, light detector 48 is offset from an axis 82a of the column of light directed through reagent/test sample mixture 97. Detector 48 is preferably a photodetector shielded from scattered light by a light barrier 108 forming an aperture 110 with a diameter of 0.152 inch. Photodetector means 48, light barrier 108, and aperture 110 are arranged to limit the light-reaching photodetector 48 to that light that is scattered along an axis 48a that lies at an angle $\theta$ with respect to the axis 82a of the light directed at mixture 97. The distance between cuvette 44 and light detector 48 is not critical.

Thus, light scattered by mixture 97 is detected at a specific angle $\theta$ by photodetector 48 which generates electrical signals proportional to the intensity of the scattered light. Photodetector 48 preferably comprises an Hamamatsu Silicon photodetector #S-1133-01. As set forth above, the photodetector is carried behind light barrier 108 having an aperture 110 of, for example, 0.152 inch diameter to prevent stray light from reaching the photodetector.

The intensity of the light scattered by the mixture in a forward direction at a given angle $\theta$ is proportional to the number of particles of given size in mixture 97, and hence, is proportional to the extent of an agglutination reaction that has taken place in the mixture. The intensity of scattered light in the forward direction is initially small since at the beginning of the reaction, the mixture will contain mostly monodisbursed particles of small size. As the agglutination reaction progresses, however, the monomers come together to form agglomerations which are larger in size. These agglomerations scatter the light that can be measured as an increase in the intensity of scattered light at the angle $\theta$ in the forward direction. The change of intensity is proportional to the change in the number of agglomerations in the mixture; and the rate of change of intensity of scattered light in the forward direction is proportional to the rate of agglutination, which, in turn, is indicative of the concentration of the biologically active substance of interest in the test sample.

It has been determined that in the invention, light detector 48 is preferably positioned to measure the intensity of the scattered light at a forward acute angle $\theta$ of about 10° to about 20°, most preferably at about 17° relative to direction 82a of the incident light. Photodetector 48 generates electric currents proportional to the intensity of the detected light, and the electric currents indicative of the light scattered at angle $\theta$, which are measured in millivolts, are transmitted to controlling and processing system 33 through a variable gain amplifier 54. Variable gain amplifier 54 is connected with microcontroller 62 through analog multiplexer 52 and analog-to-digital converter 56 over connection 54a. Analog multiplexer 52 transmits the output of photodetector 48 as amplified by variable gain amplifier 54 to analog-to-digital converter 56 which converts the amplified output to a digital signal usable by microcontroller 62 and its operating software. In addition, analog multiplexer 52 can receive a signal from microcontroller 62 over connection 52a to vary and set the gain of variable gain amplifier 54. Microcontroller 62 generates signals to set the gain of variable gain amplifier 54 in response to instructions in the system software and can vary the gain of variable gain amplifier 54 for different tests.

Figure 8:
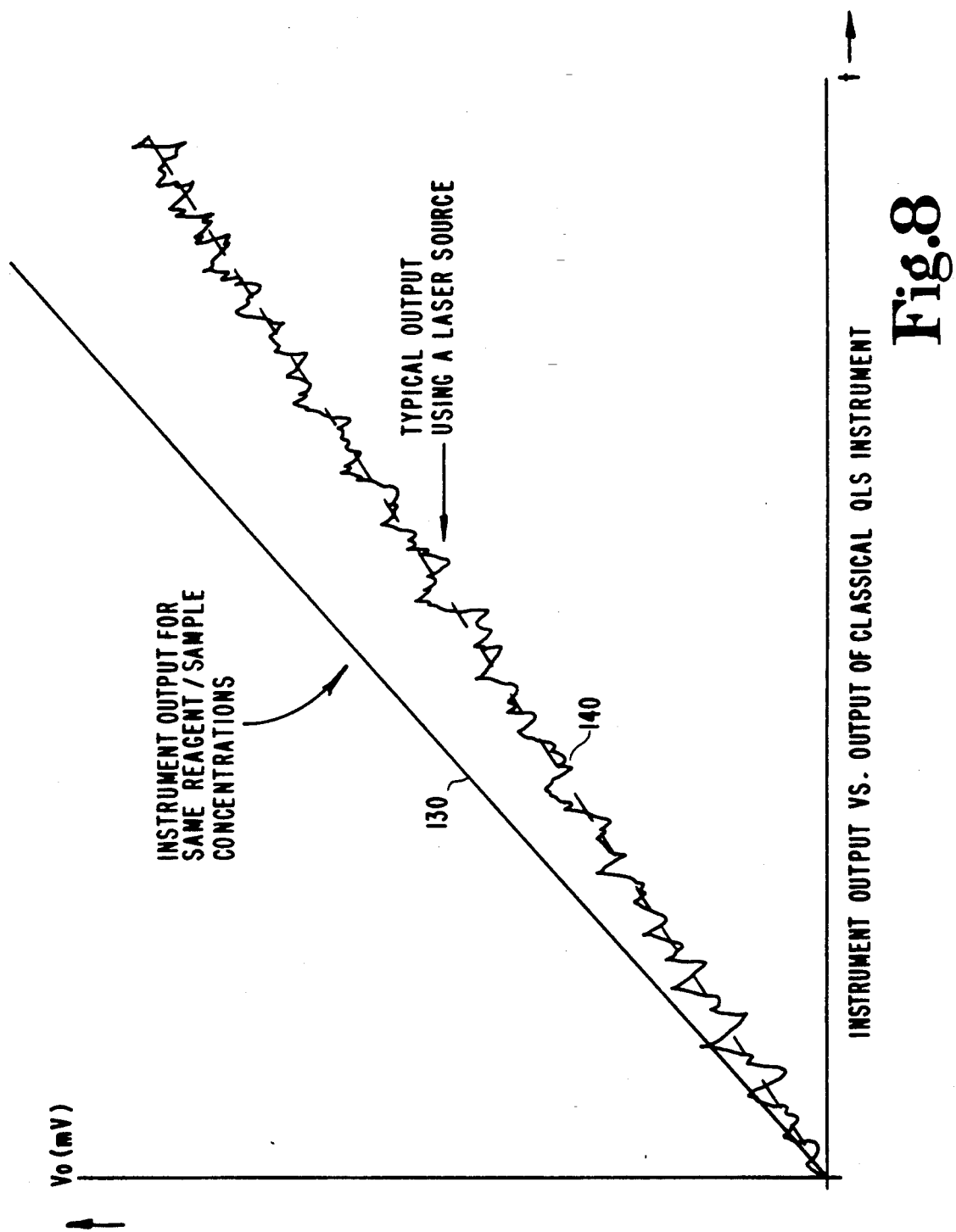
FIG. 8 is a graph illustrating the substantially errant-free operation of the system, method, and apparatus of the present invention.

The light application and measurement system of the invention provides the system with a substantially errant-free output, permitting greatly increased accuracy to be obtained in the intensity measurements performed by the system. FIG. 8 is a graph which compares the instrument output of the system of the present invention with the typical output of an agglutination immunoassay system utilizing a laser light source. As shown in FIG. 8, an output 130 of the system of the present invention is substantially free of unwanted and immaterial output variation and of increased slope as compared to an output 140 of a typical system using a laser source.

Associated with the light application and measurement system are a support 60 for mixture container 44 and an automatic pipette 46. Sample container support 60 contains a heater (not shown) to warm and maintain mixture 97 at a somewhat elevated temperature and an electrical means to effect stirring of the contents of container 44.

Processing and controlling system 33 is connected to the light application and measurement system as shown in FIG. 5. Processing and controlling system 33 preferably includes circuitry 36 to permit communication between analog inputs and outputs of light application and measurement system 32 and the digital data-processing and control system of processing and controlling system 33. Circuitry 36 includes, as previously noted, analog-to-digital converter 56, digital-to-analog converter 84, and an analog multiplexer 52. Analog multiplexer 52 is connected with the light application and measurement system over connections 54a and 88a and with a temperature control circuit 58 of the heater to warm mixture 97 in container 44 over connection 58a. Analog multiplexer 52 samples inputs comprising the amplified output of photodetector 48 over connection 54a, the current through light source 82 over connection 88a, and the input to the heater of container support 60. Analog multiplexer 52 also operates variable gain amplifier 54 in response to signals from microcontroller 62 over connection 52a to vary the amplifier gain. As shown in FIG. 5, the intensity of light source 82 may be controlled and varied by microcontroller 62 through digital-to-analog converter 84 over connection 84a; and the signal representing the output of photodetector 48 may be controlled by microcontroller 62 over connection 52a to maintain calibration of the system and to provide varied amplification for different tests in processing and controlling system 33.

Processing and controlling system 33 also includes temperature control circuit 58 connected with container-supporting means 60 including an electrical heater for container 44. The temperature control circuit includes a thermistor and diode connected to provide electrical energy to heat the electrical heater of support 60 to warm the reagent/test samples prior to the tests. The system may also include a magnetic stirring means including a magnetic bar in cuvette 44 moved by a magnetic moving means in the cuvette supporting means 60, or vibrator to effect stirring. The stirring means is operated by microcontroller 62 through a stirrer interface 68. Automatic pipette 46 is operated by microcontroller 62 through a pipette interface 50.

Controlling and processing system 33 includes an eight-bit central-processing unit such as microcontroller 62, Intel 8031 being one preferred example of such a microcontroller, a random access memory variable memory 64 having sufficient address space to store the standard curve data, and the test data on intensity measurements and time data, e.g., at least two kilobytes, and an EPROM program memory 66 with sufficient memory to store the system's operating and calibration programs, e.g., at least two kilobytes. Controlling and processing system 33 preferably also includes a replaceable test memory 106, i.e., a card-like memory device, such as the "smart cards" sold by General Instrument Corporation, capable of storing the test procedures for testing samples for a variety of biologically active substances of interest. Such a replaceable test memory permits the apparatus of this invention to be conveniently updated to perform new and improved tests for biologically active substances of interest as they may be developed.

In the preferred system, the operating program stored in EPROM program memory 66 operates CPU 62 to select and follow a test program stored in replaceable test memory 106. RAM variable memory 64 receives and stores data from light application and measurement system 32 at addresses determined by the operating program in EPROM 66 or the test program in replaceable test memory 106. Such data can represent the intensity of the scattered light detected by detector 48 and the time at which the light measurements were taken. The EPROM program memory can contain data-processing software for various test procedures, retrieving such data and calculating an output indicative of the concentration of the substance of interest being tested, in addition to software for operating and calibrating the system. The preferred controlling and processing system of this invention, however, provides the software for retrieving test data and calculating an output indicative of the concentration of the substance of interest in a replaceable test memory device.

Access to controlling and processing system 33 can be via a keyboard interface 72 and a magnetic card interface 74, and in the preferred system via a replaceable test memory 106. Mag card interface 74 permits standard curve data for different tests to be readily stored into the RAM program memory as needed, and the keyboard interface permits operator interaction and control over the system. The system further includes one or more output interfaces for controlling and processing system 33, including a thermal printer output interface 76, a 2×20 dot matrix LCD display output interface 78, and one or more additional output interfaces represented by serial port 80 to permit test results and other information to be presented to the operator and used.

The preferred apparatus of this invention is also provided with automatic pipette 46 to automatically, in response to the test procedure program, withdraw measured amounts of the sample and reagent, and to dispense the sample and reagent and signal the commencement of the test and the collection of test data.

As indicated above, during a test, analog intensity signals from photodetector 48 are converted to digital signals by analog-to-digital converter 56 and transmitted to microcontroller 62 which stores data indicative of the detected, scattered light intensity at angle $\theta$, preferably as a function of time, in RAM memory 64. This test data is then processed for comparison with standard curve data, which represents the concentration of a substance of interest. The data may be processed to determine concentration from reaction "endpoint" data (i.e., data at a specified time) and/or the rate of change of the reaction and/or the maximum rate of change of the reaction, as determined from the measurements of the scattered light intensity over time. RAM memory may be provided, from mag card interface 74 or replaceable test memory 106, with standard curve data for any one or all of such determinations. The comparison and all necessary calculations are performed by microcontroller 62 using a program stored in EPROM 66 and/or preferably replaceable test memory 106 and are outputted to a printer 120 via thermal printer interface 76, or to an LCD display 122 via LCD display interface 78, respectively.

Thus, as indicated above, software for any one or more test procedures for a particular substance of interest can be inserted into the preferred embodiment of the apparatus with a replaceable test memory 106, and standard curve data for a particular substance of interest and associated particular reagents can be inserted into RAM memory 64 by the operator via mag card interface 74 before testing. Thus, the system of this invention can be used for new immunoassay tests as they are developed. The manner in which the standard curve data is developed for a test will be described more fully hereinafter.

Figure 7:
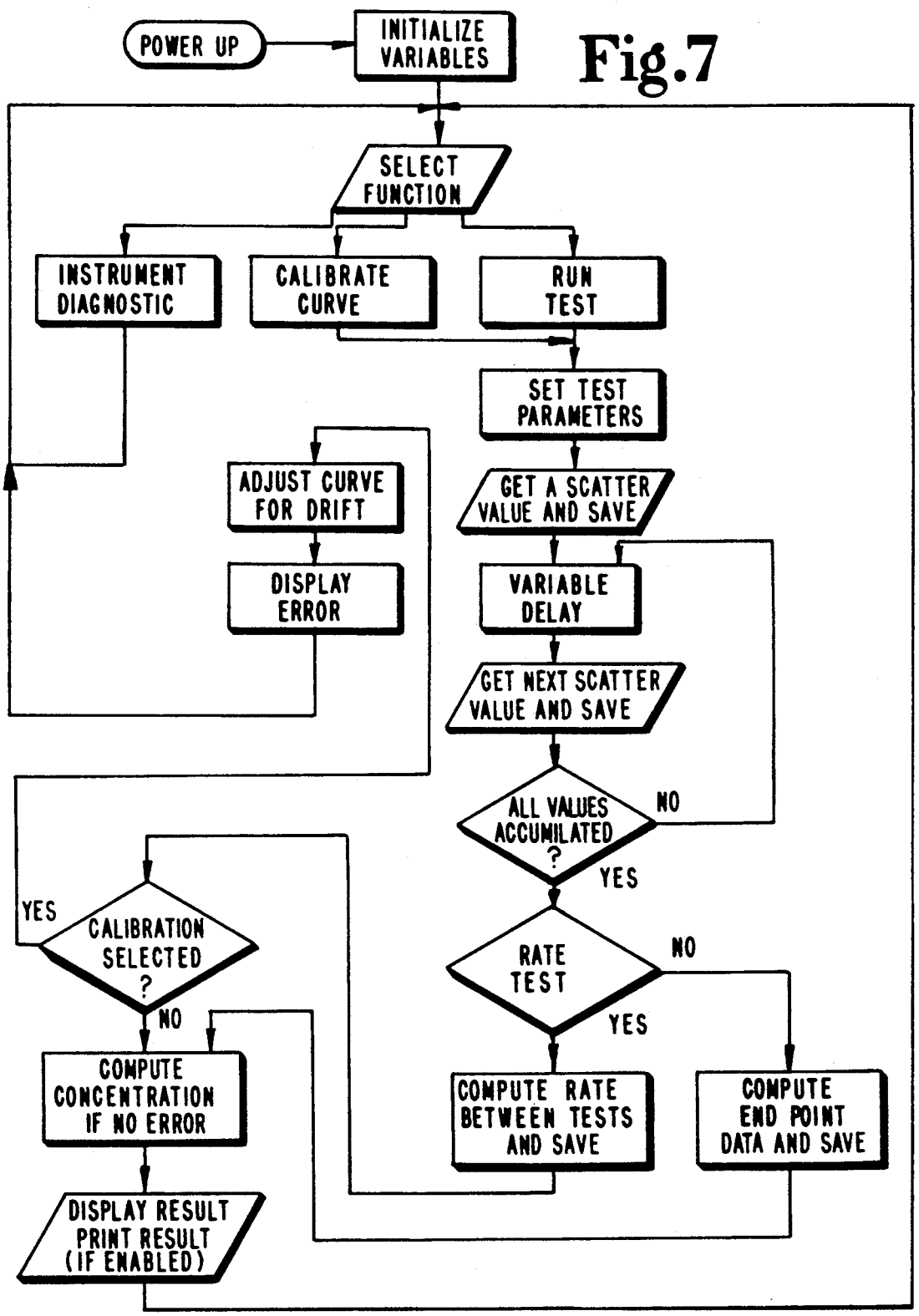
FIG. 7 is a flow chart illustrating the operation of the system of FIG. 5.

The system and process for performing an agglutination immunoassay to measure the concentration of a biologically active substance of interest is further illustrated by the flow chart in FIG. 7.

After initializing microcontroller 62, the operator, using keyboard 72, selects from a menu presented on LCD display 122, for example, either an instrument diagnostic test, a calibration test, or an actual agglutination test. Programs for operation of the microcontroller 62 are stored in EPROM 66.

With the selection of the instrument diagnostic tests, microcontroller 62 operates light application and measurement system 32 to determine whether light source 82 is continuing to operate properly. Basically, in the instrument diagnostic test, light source 82 is operated with a standard test cuvette inserted in the instrument. The standard test cuvette contains a suspension of particles in fluid which has a known and predictable scattering of light. During the instrument diagnostic test, the light scattered by the standard test cuvette is sensed; and its intensity is compared with a "standard" light intensity through the standard test cuvette which was adjusted at the factory following manufacture of the system measured and stored in the system. In addition, the current through light source 82 is sensed; and its value can be compared with "standard" or earlier values to confirm proper operation of light intensity control 86 and to determine if there is some malfunction of illuminating means 42. Such a test confirms that the light application and measurement system is operating properly. If the intensity of the resulting light, or light source 82 has deviated from its standard intensity, microcontroller 62 generates operating signals directed over connection 52a to light intensity control 86 to correct for the deviation. The program for the instrument diagnostic test contains data for comparison and instructions and data for providing corrective adjustments and generates a digital signal to drive digital-to-analog converter 84 and provide the corrective output to light intensity control 86.

In the calibration curve test, a cuvette containing a standard test fluid, that is, a test fluid containing sensitized particles having their surfaces sensitized with antibodies or antigens that agglutinate in a known and predictable standard manner, is placed into the system. An agglutinator for the standard test fluid of a known concentration is mixed with the test fluid, and a test is conducted of the resulting agglutination reaction. The operating and test procedure programs stored in EPROM 66 and replaceable test memory 106 begin reading the intensity of the scattered light, preferably in a timed series of measurements. That is, with the selection of a calibration test by the system operator, a menu prompts the system operator to enter the parameters of the calibration test. The parameters entered by the system operator with keyboard 72 provide data to the system to permit it to run the calibration test and recover the appropriate calibration test procedure and "standard" for comparison purposes.

As shown in FIG. 7, after the test parameters have been entered into the system, the program in EPROM 66 reads the digitized signal indicative of the light scattered along angle $\theta$ by the agglutination of particles taking place in the test fluid and the time of the measurement and stores the first scatter value data corresponding to the scattered light intensity and time of its measurement in RAM 64. After a variable time delay determined by the test parameters entered by the system operator, microcontroller 62 measures again the scattered light output of light application and measurement system 32 and the time in which the measurement is taken and stores the second scatter value data in RAM 64. If all values of scattered light required by the test procedure have not been determined, another scattered light value is measured after a variable time delay; and the measurement and the time at which the measurement is taken are stored, and this process iterates until all values of scattered light required by the test procedure have been measured and stored with the times of their measurement. If a rate test has been selected among the test parameters, microcontroller 62 computes the rate, or rates, of agglutination and stores the rates in RAM variable memory 64.

With the selection of calibration curve, the first and second values of scattered light and the rate of agglutination between the times of the first and second measurements are compared with the appropriate standard curve data which has been stored in RAM 64. Microprocessor 62 determines if there is any difference between the calibration test data and the standard curve data and, if so, adjusts the data representing the standard curve stored in RAM 64 for the difference and displays the "error" at LCD display 122. Thus, with the calibration curve test, the system can be adjusted daily for drift due to environmental changes and aging and for differences due to operator technique.

If the operator selects an actual test, a menu from EPROM 66 is displayed in LCD display 122, prompting the operator to enter an identification of the test to be run. Microcontroller 62 uses the data entered by the system operator with keyboard 72 to identify the tests to be run and recover the test procedure program from, preferably, replaceable test memory 106, and displays from replaceable test memory 106 a menu of test parameters specific to the selected test. The system will, if necessary, prompt the system operator to enter data for the test to be run if it is not present in the system; such data may be entered by the system operator either with keyboard 72 or mag card interface 74.

After entry of such data, microcontroller 62 begins the test by operating the automatic pipette and measuring the light scattered along angle $\theta$ by the agglutination reaction taking place in cuvette 44, and preferably the time of the test, and stores the first data on the scattered light value and time in RAM 64. After a variable delay determined by the specific test being conducted and the parameters specific to that test, microcontroller 62 will be prompted by the operating program in EPROM 66 to read again the scattered light value from along angle $\theta$ as a result of the agglutination reaction taking place in cuvette 44. The data on the second reading of scattered light value and the time of the reading are also stored in RAM 64. If all values of scattered light required by the test procedure have not been determined, the next scattered light value is determined after a variable time delay; and the scattered light value and the time at which it occurred are stored in RAM 64, and this process continues until all scattered light values required by the test procedure have been determined.

If a rate test is part of the specific test being conducted, the operating program stored in EPROM 66 causes microprocessor 62 to recover the stored data on the scattered light values and the stored data on the times of each of the scattered light values and to compute a rate of change between each of the scattered light measurements. These rates of change, pursuant to the operating program stored in EPROM 66, or in replaceable test memory 106 are stored in RAM 64. This process may be repeated a number of times corresponding to the test parameters specific to a test being conducted.

In this mode of operation, microcontroller 62, pursuant to the operating program stored in EPROM 66, or in replaceable test memory 106, compares the stored data from the actual test with the standard calibration curve data for that test which is stored in RAM 64, and determines from the comparison the concentration of the biologically active substance of interest that was contained in the test sample being tested in cuvette 44. Microprocessor 62 stores this concentration in RAM 64 and displays the result on LCD display 122 and, if selected, prints the results on printer 120. The determination of concentration can be accomplished by comparing data at a specified time during the test, e.g., the reaction "end-point", or by comparing a rate of change of such data during the test, e.g., the maximum rate of change, or by comparing rates of change of such data at various times, or any combination thereof, if desirable.

The number of tests which can be run by the machine are limited only by the storage capability of its memories. As the immunoassay system of this invention is further developed by the addition of more specific tests, the memories may be expanded to provide address space sufficient to store the data corresponding to each of the specific tests developed. In addition, in the invention, reagents to be used with the system are accompanied by mag cards, or other information, permitting standard curve data for each manufactured lot of reagent to be entered into the system to prevent the system from becoming inaccurate as a result of differences in the polymer particles and reagents through manufacturing differences.

With the system of the invention, a test can be performed rapidly and accurately. The equipment is smart, somewhat manual, but generally user-friendly such that it does not require highly skilled personnel to operate it. The equipment is also relatively low in price and compact in size such that it can readily be used in a cost effective manner in doctors' offices, small labs, or other low-volume operations.

A key element in the immunoassay system of the invention is the polymeric particles used as the carrier particles in the system. The remarkable and unexpected sensitivity of the system is the result of the ability of the system to quickly detect small changes in the mean particle size used in a given assay as a result of linking or agglutination of sensitized particles in the presence of the specific agent which causes the particles to be linked or agglutinated. In order to detect such linkage at an early stage, the particles must be as uniform in size as possible, e.g., 0.18 micron ±0.01 micron, and be adapted to interact with the light from the light source. Specifically, the size dispersion of the particles must be carefully controlled to be within a very narrow size distribution (i.e., C.V.=±2% for each particle size used), and to permit accurate intensity readings to be obtained. It is important that the particles be made of materials which are capable of scattering light and which do not react non-specifically in body fluids.

The primary components of such polymer particles can be, for example, a vinyl aromatic monomer, and a vinyl acrylate ester monomer. The vinyl aromatic monomer can be styrene, vinyl toluene or t-butyl styrene or mixtures thereof. Preferably, the vinyl aromatic monomer can be styrene. The vinyl acrylate ester monomer can be a monomer having pendent alkyl ester group of from one to six carbon atoms. Preferably, the vinyl acrylate ester monomer can be methyl, ethyl, propyl, n-butyl, s-butyl, or other versions of the acrylate monomer or versions of a methacrylate vinyl unit, such as methyl methacrylate, ethyl methacrylate, propyl methacrylate, and the like. Most preferably, the vinyl acrylate ester monomer can be n-butylacrylate.

The polymer particles of this invention are prepared by conventional emulsion polymerization methods which may include either batch or continuous addition polymerization or multiple step polymerizations. Optionally, oil-soluble or water-soluble initiators, and emulsifying agents, or buffer systems to control the pH may be added. The emulsifying agent suitable for stabilizing such particles can be both ionic or non-ionic emulsifiers. Of the ionic surfactant, those such as sodium dodecyl benzene sulfonate, alkyl diphenyloxide disulfonate, and sodium dihexylsulfosuccinate are suitable. In these systems, water is the continuous medium; and a synthetic emulsifier can be used to stabilize the particle.

In one approach, the emulsifier is of such a concentration that micelles form which solubilize a certain quantity of monomer, the majority of which is dispersed in small droplets. The addition of an initiator facilitates polymerization in these micelles which, in turn, imbibe more monomer. The micelles serve as the locus of polymerization of more monomer as the latter diffuses to these sites, the monomer droplets thus acting as a reservoir for this purpose.

Optionally, a seeded emulsion polymerization may be used. Here a concentration of small seed particles can be used as sites for further growth by the addition of more monomer, thus forming the copolymer. The temperature of the polymerization is about 70° C. to about 95° C.

Water-soluble initiators suitable for inducing polymerization of the modifying monomer onto the copolymer can include, but are not limited to, certain inorganic oxidizing agents such as hydrogen peroxide, sodium perborate, and various persulfates such as sodium persulfate or potassium persulfate; preferably, sodium persulfate is used. Preferably, sodium persulfate is used in the amount of about 0.1 to 1.0 weight percent of the copolymer, preferably about 0.2 to about 0.5 weight percent.

Typically, the vinyl aromatic and vinyl acrylate ester monomers are combined in a weight ratio of about 1:3 to 3:1 vinyl acrylate ester monomer to vinyl aromatic monomer to form a copolymer. The preferred weight ratio of vinyl aromatic to vinyl acrylic ester is 1:1, based on the weight ratio of the two monomers.

The particles can be sensitized by a protein-binding-modifying monomer, which can be attached to the particles by copolymerizing it with the bulk of the other monomers comprising the polymer particles or copolymerizing it with a small fraction of the total monomer charge as, for example, a coating on the surface of a particle.

The weight fraction of the protein-binding-modifying monomer is defined by the efficiency with which it binds a protein. Generally, the protein-binding-modifying monomer is added to the copolymer in an amount ranging from about 0.5 to about 10 weight percent of the copolymer. Preferably, acrylic acid is used as the protein-binding-modifying monomer and is preferably used in a range from about one to about three weight percent of the copolymer.

In the polymerization process, the size can be defined by either the amount of emulsifier used or a seed particle concentration. The seed concentration is calculated as the quantity necessary to provide the preferred particle size. Typically, the particles are about 0.1 to 1 micron; however, for the light-scattering system of the invention, the preferred size of the particle is 0.18 micron.

In the system of the invention, the concentration of a biologically active substance of interest is determined by the light-scattering properties of particles as they agglutinate. The ability of the polymer particles to scatter light as they agglutinate is related to their refractive index. The polymer particles, however, must not react non-specifically with body fluids. The polymer particles adapted for use with this invention must thus combine these properties.

It proved to be easiest to detect an agglutination reaction when the vinyl aromatic monomer content of the particles was high because of its favorable refractive index, but then the particles interacted non-specifically with body fluids. Conversely, when the vinyl acrylate ester monomer content of the particles was high, the particles did not readily interact non-specifically with the body fluids; but the aggregation reaction was more difficult to detect because of the lower refractive index of the vinyl acrylate monomer. Thus, balancing the need for easy detection of the agglutination reaction and the need for the particles to be inert to non-specific interaction with the body fluids, the weight ratio of 1:1 vinyl acrylate ester monomer to vinyl aromatic monomer was found to provide significant and unexpected advantages in the invention.

The polymer particles must also be treated to ensure that sufficient quantities of biologically active substances of interest, such as antigens or antibodies, are irreversibly attached to their surfaces.

Once prepared, a desired antibody or antigen can be bound to the polymer particles via an intermediate route known as the carbodiimide technique. Although the carbodiimide technique is preferred, any of the coupling techniques known in the art to facilitate the binding of the protein to a particle can be used. Carbodiimide is a group of symmetrical anhydrides of urea, having the composition $HN{=}C{=}NH$. The hydrogens can be substituted with other substituents to give N,N'-disubstituted carbodiimides. The acid catalyzed addition of water to these carbodiimides, i.e., hydration, to form ureas, permits the synthesis of amide and peptide bonds. Peptide bonds arise by the elimination of water, i.e., condensation between two suitably protected amino acids, one containing only a free carboxyl and the other only a free amino group, thus restricting synthesis to the formation of a specific amide bond.

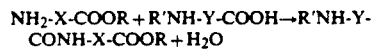

This condensation can be effected by means of dicyclohexylcarbodiimide (DCC) as taught in "A New Method for Forming Peptide Bonds," *J. Amer. Chem. Soc.*, 77 (1955) 1067–1068, Sheehan, J. C., Hess, G. P. and in "The Use of Dicyclohexylcarbodiimide in The Synthesis of Peptides," *Chem. Ind.* (London) (1955) 1087–1088, Khorana, H. G. The reaction is presented as follows:

where
$R' = C_6H_{11}$;
$R' =$ the support;
$R'' =$ protein backbone; and
$CON =$ covalent linkage between the support and protein.

This procedure is not sensitive to moisture and can therefore be carried out in aqueous media; whereas, procedures involving mixed anhydride formation must be carried out under anhydrous conditions. The temperature and the nature of the amine and solvent influence the yield of amide, but that of the acid has little effect.

Although DCC was first used as a means for condensation, other carbodiimides have been widely used, e.g., EDC, 1-ethyl-3-(3-dimethyl-aminopropyl) carbodiimide hydrochloride, and CMC, 1-cyclohexyl-3-(2-morpholinoethyl) carbodiimide metho-p-toluene sulphonate, have been successfully used. N,N'-dicyclohexylurea, the urea formed from DCC, has a very low solubility in most organic and aqueous solvents and is usually separated by crystallization. The corresponding urea derivatives of EDC and CMC, however, are soluble in water and are easily separated from the peptide. Therefore, EDC and CMC are preferred when a synthesis is performed in aqueous media with one reactant immobilized on a support. The synthesis is a convenient one-step procedure with no crystallizations and unreacted starting material; and reaction by-products are simply washed away, leaving the antibody/antigen bound by an amide bond to a support or, as applicable in this instance, the particle.

The surfaces of the polymer particles can be further chemically treated in specific ways depending on the particular tests to be conducted, as described in detail in the following example of specific immunoassays of the invention.

The particles must also be treated to ensure that spontaneous, non-specific agglutination does not occur while the desired specific agglutination is not unduly inhibited. This has been accomplished in the case of a blood serum test sample by the addition of a halogen-substituted carboxylic acid to the reaction mixture as described in U.S. Pat. No. 4,536,478, the disclosure of which is hereby incorporated by reference.

A more complete understanding of the invention can be obtained by reference to the following example of the new method of testing for Theophylline that is provided by this invention. The following Theophylline-testing method is illustrative of one application of the invention and is not limiting.

As noted above, the present invention provides a highly sensitive system and method which is effective in providing an accurate quantitative measurement of the concentration of many biologically active substances of interest in fluid samples reliably and at relatively low cost. The present invention provides sensitivities of from 1,000 to 1,000,000 times greater than agglutination-testing systems currently in use.

EXAMPLE

Theophylline Immunoassay

As noted above, an agglutination test for Theophylline is preferably conducted in the indirect format and includes providing a reagent solution, comprising at least a buffer and an anti-Theophylline antibody and a reagent suspension, comprising a buffered suspension of sensitized, uniformly sized copolymer particles with attached Theophylline antigen.

The reagent solution is provided as follows:

A. Preparation of Agglutination Reaction Buffer
 1. Materials, Stated in their Final Concentrations in the Buffer
   a. $Na_2H/NaH_2PO_4$, 0.1M, pH 7.4.
   b. NaCl, 0.15M.
   c. BSA, 0.1%.
   d. Polyethylene Glycol(PEG)8000, 2.7%.
   e. $NaN_3$, 0.1%.
   f. Monoclonal anti-Theophylline antibody, approximately 320 uL per liter of buffer.
 2. Protocol
   a. Prepare(PEG)8000 as a ten percent w/v stock solution in deionized water.
   b. Prepare $Na_2H/NaH_2PO_4$, NaCl, BSA and $NaN_3$ in 500 mL deionized water then q.s. to 730 mL with deionized water. Adjust pH to exactly 7.4.
   c. Add 270 mL of the ten percent (PEG)8000 solution dropwise to above preparation, with stirring.
   d. Add Monoclonal anti-Theophylline antibody. Approximately 320 uL of antibody per liter of buffer will be required; however, the exact amount must be titrated to match the activity of the individual Theophylline Particle Reagent (TPR) batch, which is prepared as set forth in D below. The reaction buffer is matched to the TPR activity to provide the desired standard curve data in a quantitative agglutination immunoassay system.

Carboxy-modified copolymer particles, prepared as described above, and having a diameter of 0.18 micron are cleaned and prepared as a nine percent suspension in deionized water as follows:

B. Preparation of Cleaned Nine Percent Particle Suspension
 1. Materials
   a. CML particles, 0.18 um diameter.
   b. Mixed cationic/anionic ion exchange cleaning resin (BioRad AG 501-X8).
   c. Deionized filtered water.
   d. Sintered glass filter, 50 mL glass beaker, 250 mL glass sidearm, flask, stir bar, stir plate, watch glass.
 2. Protocol
   a. Dilute CML particles to a suspension of approximately nine percent solids content with deionized water.
   b. Mix CML particle suspension with ion exchange resin: ½ weight of CML solids per unit weight of resin in a 50 mL glass beaker.
   c. Add magnetic stir bar, cover with a watch glass, stir gently for two hours at room temperature.
   d. Place in sintered glass filter on 250 mL glass sidearm flask and slowly filter into flask by opening vacuum line to flask gradually, until suspension just barely moves through filter into flask.
   e. Transfer filtrate to brown glass container, seal tightly, and store at room temperature until ready to use.

Following preparation of the Nine Percent Particle Suspension, the reagent suspension is provided as follows:

C. Preparation of the Theophylline-8-Hydroxypropyl Amine (THPA) component of the Second Reagent
 1. Materials
   a. 1,3-diamino-2-hydroxy propane (DAP).
   b. Theophylline-8-butyric acid lactam (TBAL).
   c. Dioxane, spectrophotometric grade.
   d. Buffer: $Na_2CO_3$, 0.1M, pH 8.5. After preparation of buffer and adjustment to pH 8.5, container should be flushed with $N_2$ gas and tightly capped to prevent atmospheric $CO_2$ from causing rise in pH. Notwithstanding the above, the pH of the $Na_2CO_3$ buffer should be checked and readjusted as necessary prior to each use.
   e. Ice bath, brown glass reaction vessel with tight seal, magnetic stirrer and stir bar appropriate to size of reaction vessel.
 2. Protocol
   a. Dissolve 200 mg DAP in 45 mL buffer (DAP solution).
   b. Dissolve 1 mg TBAL per 1 mL Dioxane.
   c. Mix 10 mL of DAP solution with 18.5 mL of $Na_2Co_3$ buffer in reaction vessel, add a stir bar and cool mixture to 4° C. in an ice bath on a magnetic stirrer.
   d. Bring mixture to a fast stir and add 1.5 mL TBAL dropwise to reaction mix.
   e. Reduce stirrer speed and maintain 4° C. temperature with slow stirring for a minimum of four hours.
   f. After a four-hour minimum, reaction mix is diluted 1:4 with cold buffer and stored at 4° C. until used. This product remains useful for subsequent reactions for at least six months at 4° C.
   g. Reaction product (THPA) may be checked for presence of Theophylline by reading optical density at 274 nm against a buffer blank. Range of $OD_{274} = 0.65-0.80$.

D. Preparation of the Theophylline Particle Reagent (TPR)
 1. Materials
   a. Cleaned CML particles, nine percent suspension in D.I. water, from Protocol B.2. above.
   b. THPA, from Protocol C.2. above.
   c. EDC, 1-ethyl-3-(3-dimethyl-amino propyl) carbodiimide.
   d. Reaction buffer, $Na_2CO_3$, 0.1M, pH 8.5.
   e. Wash buffer, $Na_2H/NaH_2 PO_4$, 0.1M, pH 7.4; NaCl, 0.15M; Tween 20, 0.05 percent; $NaN_3$, 0.1 percent.
   f. Brown glass bottle of 50 mL capacity, with cap, containing stir bar.
   g. Disposable syringe filter, 0.22 um, cellulose acetate, on 5 mL plastic syringe.
 2. Protocol
   a. Filter 5 mL of the about nine percent suspension of CML particles through 0.22 um syringe filter into a clean glass container to ensure uniform single particle dispersion.

b. In 50 mL brown glass bottle, mix 12 mL of the Na$_2$CO$_3$ buffer, 4 mL of the filtered nine percent CML particles, and 2 mL of THPA. Place on magnetic stirrer with medium stirring.
c. Dissolve 336 mg EDC in 3 mL of deionized water.
d. Turn stirrer under reaction vessel to fast stirring and add EDC solution dropwise to vessel. After addition, continue fast stirring for 60 seconds, then turn down to slow stirring.
e. Allow reaction to continue for 18 hours at room temperature (22°-25° C.).
f. After 18 hours, remove reaction vessel from stirring Aliquot 10.5 mL of reaction mix into each of two 50 mL polypropylene round bottom centrifuge tubes and centrifuge at 26,890 xg for 30 minutes with centrifuge refrigeration set for 4° C.-12° C.
g. Resuspend in 10 mL wash buffer.
h. Repeat three times with final resuspension to the original 21 mL total combined volume; transfer to a clean brown glass bottle. Wash buffer is also storage buffer.
i. Store tightly capped at 4° C. for two to three days to permit stabilization before using.

In the preparation of the Theophylline particle reagent, the preferred final volume of reaction mix is 21 mL as described, but final volumes of 15 mL to 26 mL may be used with reduced effectiveness. Multiples of this mix may be prepared with equal effectiveness (e.g., ½x, 2x, 4x) as long as similar proportions of reagents are prepared. In addition, concentrations of EDC from 10 mg/mL upwards are effective, but 16 mg/mL gives maximum activity of TPR in assay. Further, the proportion of THPA indicated above is believed to be optimal; but the proportion of THPA is effective from less than one tenth that described to ten times that described.

During a test with the system of this invention, a serum test sample and reagent solution and reagent suspension are then mixed and the concentration of Theophylline in the test sample is determined as follows. Place 1.25 mL of the agglutination reaction buffer (the first reagent, prepared by Protocol A.2. above) in a 4 mL square polystyrene cuvette (44 FIG. 5) and warm to 37° C. (If the cuvette is in the preferred apparatus of this invention, it will be warmed to 37° C. automatically by the apparatus of this invention.) Add ten microliters of the human serum test sample to the agglutination reaction buffer and mix thoroughly and quickly by, for example, shaking the cuvette. (If the cuvette is in the preferred apparatus of this invention, it will be stirred automatically by magnetic stirring means or a vibrator.) Then add and mix with above mixture 25 microliters of the Theophylline Particle Reagent (the second reagent, prepared by Protocol D.2. above). The agglutination reaction will then proceed and can be measured by any apparatus which has been adapted for measurement of scattered light, which may be used to determine the concentration of Theophylline in the test sample. Preferably, such apparatus should be able to control temperature, able to determine rates of reaction or reaction end-points, able to internally store standard curve data, able to internally calibrate that standard curve, and able to access that data to determine the concentration of Theophylline in the sample.

Figure 9:
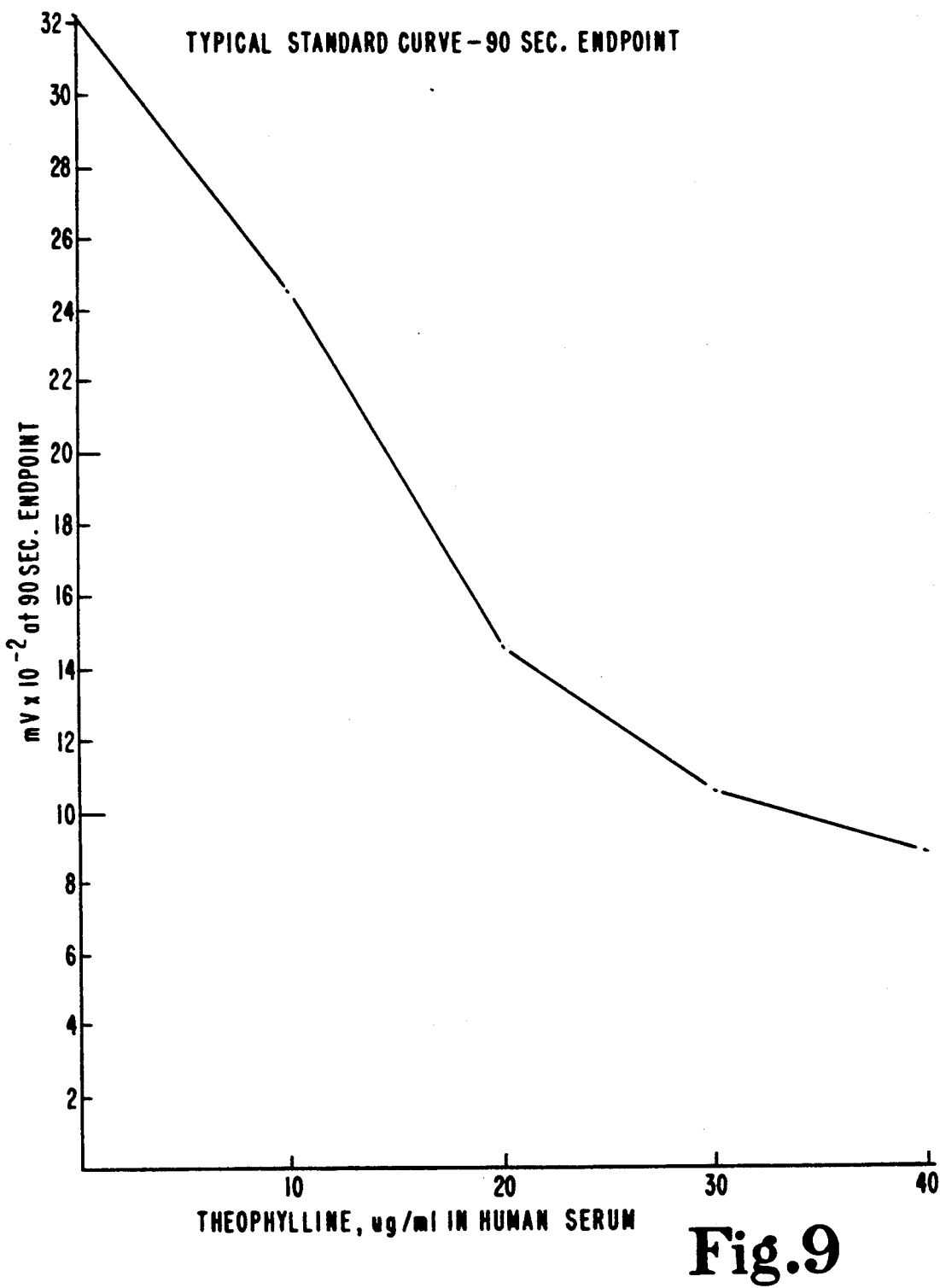
FIGS. 9, 10, and 11 illustrate typical standard curve data for biologically active substances of interest. Specifically.

For optimal sensitivity and speed, this test is conducted in the apparatus of this invention by placing the cuvette in the apparatus after the first reagent or Agglutination Reaction Buffer and the human serum test sample have been mixed in the cuvette. It is understood that the apparatus will have stored in its memory standard curve data corresponding to that shown in FIGS. 9, 10, and/or 11. This standard curve data will have been generated from tests with the system, method, and apparatus of this invention of serum samples containing from 1 to 40 micrograms of Theophylline per milliliter of serum. In addition, the apparatus will preferably have been previously calibrated by the program stored therein to adjust the standard curve data stored therein for any variables that may affect its accuracy. The operator will then instruct the apparatus to select an actual Theophylline test from the menus presented by the apparatus and will enter any information for the test that is requested by the apparatus.

The Theophylline Particle Reagent, the reagent suspension, is then collected and added to the cuvette in the apparatus by its automatic pipette and mixed thoroughly and quickly by its magnetic mixing means. The apparatus will automatically "START" the test, and the apparatus, operating from the program stored therein, reads the output of the photodetector in millivolts and the time of the measurement. For example, the apparatus can read the photodetector output at 90 seconds into the test and compare the millivolt value with the calibrated standard curve data, FIG. 9, to determine the concentration of Theophylline in the serum test sample. If, for example, the multivolt output of the photodetector is 1400 millivolts, the concentration of Theophylline in the test sample will be 22 micrograms per milliliter. If a rate test is used to measure or confirm the measurement, the apparatus will, for example, measure the millivolt output of the photodetector at five-second intervals, calculate the slope, and compare the calculated slope with the standard curve data of FIG. 10 in determining the concentration of Theophylline in the test sample. With the Theophylline test of this invention, it is believed that maximum reaction rate data can provide a very reliable determination of the concentration of Theophylline in the test sample. Accordingly, the maximum rate of change of the data (or slope) can be calculated and compared with the maximum rate data of FIG. 11 in determining the concentration of Theophylline in the test sample.

Figure 10:
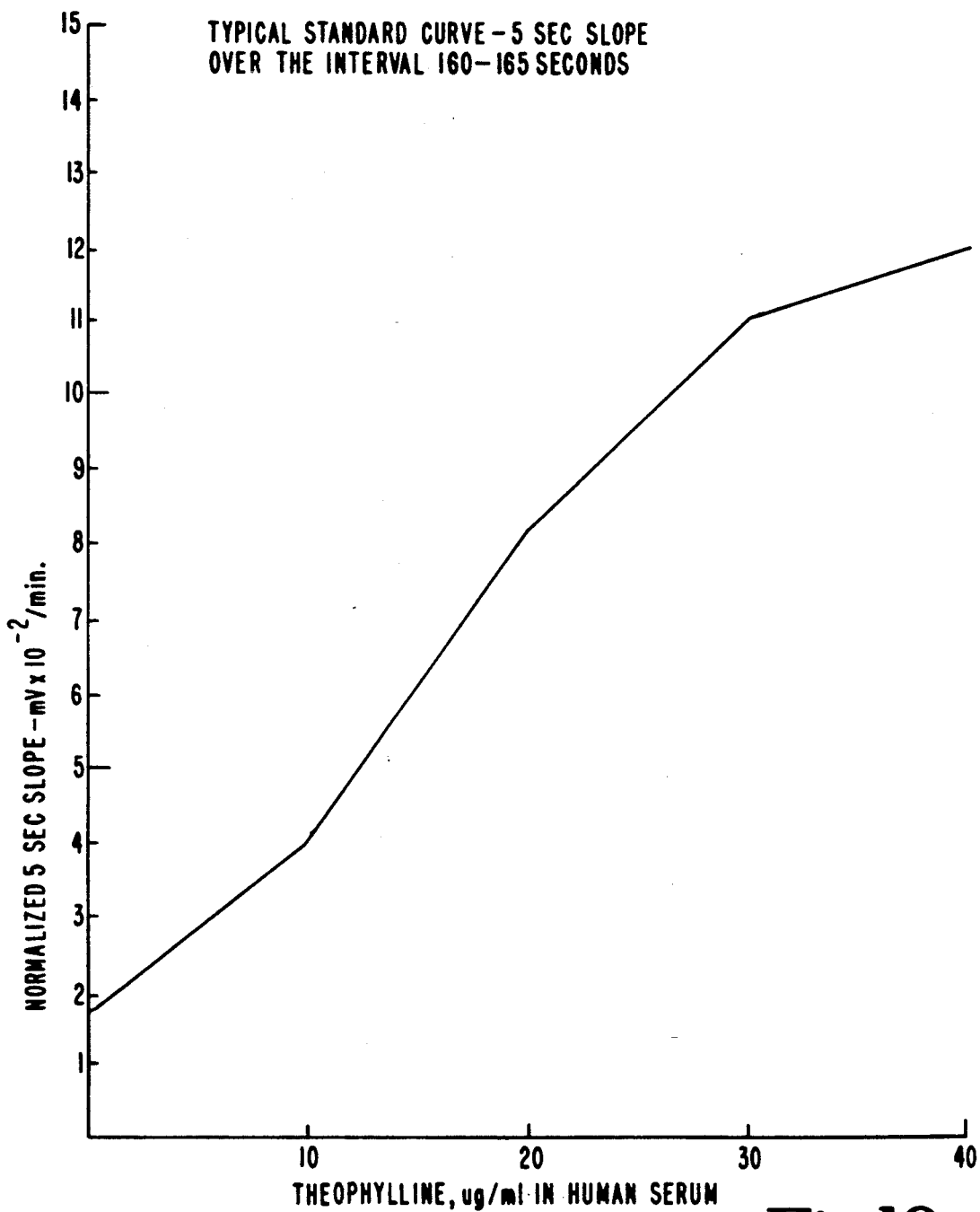
Figure 11:
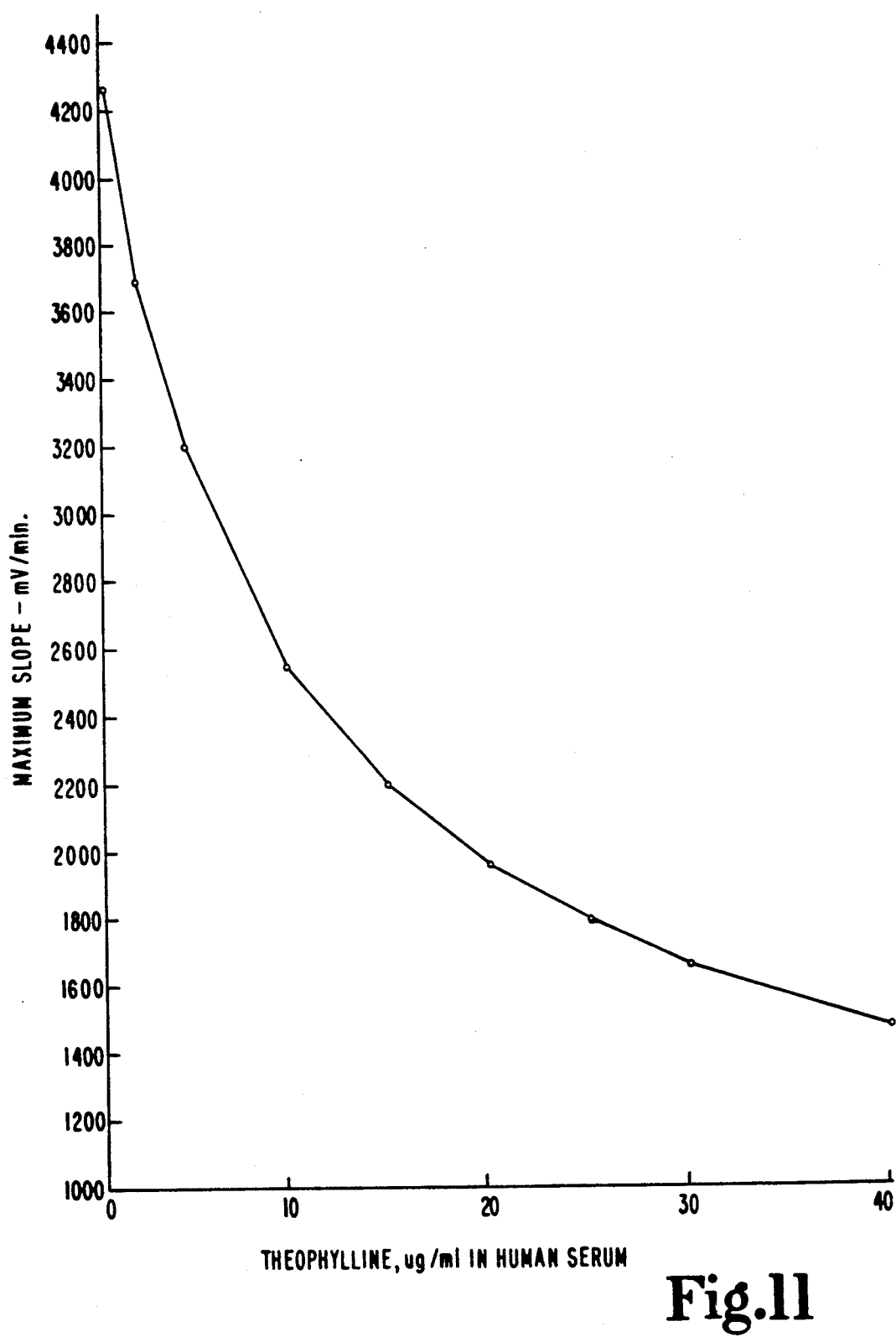

In the apparatus, the reaction and subsequent standard curve may be determined and stored for reaction times usually from 30 seconds to five minutes when using mV/time as parameters. Within any period during the reaction, the mathematical slope between any two readings of the instrument, which may occur at any time interval, but, preferably, occur five seconds apart, may be normalized to millivolts/min. and plotted verses concentration and will yield a useful standard curve (FIG. 10). The maximum slope determined from such data can also be a particularly reliable measure of the concentration of Theophylline as a result of this invention (FIG. 11).

While what has been described constitutes a presently preferred embodiment of the invention, it should be recognized that the invention could take numerous other forms. For example, the system and method of the invention are not limited to carrying out the specific test for Theophylline described herein, but can be used to perform numerous other tests which have been developed or may be developed in the future. It should be understood, accordingly, that the invention should be limited only by the scope of the following claims.

We claim:

1. Apparatus for conducting an agglutination immunoassay test, comprising:
   a light application and measurement system adapted to receive a container for a fluid sample to be tested and to direct a column of high-intensity, substantially monochromatic non-laser light at the fluid sample container, to detect light intensity scattered outside of the column of light and travelling from the fluid sample container in a forward direction at an acute angle to the column of light, and to provide a high, errant-free output at a very low scattered light intensity; and
   a processing and controlling system adapted to use the errant-free output to generate and store data correlating the output of the light application and measurement system with the concentration of a substance of interest in the fluid sample container, to store standard curve data for the substance of interest, and to determine, from the data generated from the output of light application and measurement system and the stored standard curve data, the concentration of a biologically active substance of interest in the fluid sample container.

2. The apparatus of claim 1 wherein the light application and measurement system comprises:
   a transparent container for supporting a mixture of fluid sample and one or more reagents, said reagents including at least a buffered suspension of uniformity mixed polymeric particles providing good light refraction and surfaces sensitized by surface function groups to permit the attachment of antigens or antibodies of the substances of interest;
   means for illuminating said mixture through said transparent container with high-intensity light, said illuminating means including a light source and means for directing the light from said light source at said mixture in said container;
   a detector for detecting light scattered by the mixture in a forward direction at an acute angle of from about 10° to about 20° relative to the path of said illuminating light; and
   wherein said processing and controlling system comprises: means for generating digital test data proportional to the intensity of said detected scattered light;
   a memory for storing the digital test data representing the intensity of the detected scattered light and for storing other data representing the concentration of the substance of interest as a function of scattered light intensity;
   data-processing means for comparing the stored test data with the other data in the memory and for determining the concentration of the substance of interest; and
   output means coupled to said data-processing means for providing a quantitative measure of the concentration of said substance of interest in said test sample.

3. The apparatus of claim 2 wherein said illuminating means comprises a high-intensity, light-emitting diode and control means for controlling the intensity of said light-emitting diode.

4. The apparatus of claim 3 wherein said illuminating means further includes a collimator directing light from said light-emitting diode at said mixture in said transparent container, and an aperture plate positioned between said light source and said collimator.

5. The apparatus of claim 3 wherein the wavelength of said light is approximately 660 nanometers.

6. The apparatus of claim 3 wherein said control means includes a controlled current source coupled to said light-emitting diode, means for controlling the current source of said light source, and means for monitoring the intensity of said light source and for controlling said current source to maintain the intensity of said light at a selected level.

7. The apparatus of claim 6 wherein said means for monitoring the intensity of said light source and for controlling said current source comprises a light intensity detector positioned to receive light from said light source and adapted to provide a signal for controlling the current source to maintain the intensity of said light at said selected level.

8. The apparatus of claim 2 wherein said detector comprises a photodetector.

9. The apparatus of claim 8 wherein said detector further includes an aperture plate between said container and said photodetector to limit the light reaching the photodetector to light travelling at an acute angle offset from the light direction of said collimator.

10. The apparatus of claim 2 wherein said memory comprises a random access memory, and wherein said data-processing means comprises a microcontroller and a second memory that stores an operating program for said apparatus.

11. The apparatus of claim 2 wherein said memory also includes a replaceable test memory that stores information for determining the known concentration of a substance of interest as a function of scattered light intensity.

12. The apparatus of claim 10 and further including means for inputting the standard curve data of any of a plurality of substances of interest into said random access memory.

13. The apparatus of claim 2 wherein the sizes of said polymeric particles are about 0.10 micron to about 0.40 micron.

14. The apparatus of claim 13 wherein the size of said polymeric particles is 0.18 micron ±0.01 micron.

15. The apparatus of claim 2 wherein said memory also stores further data representing the rate of change of the value of the digital test data with time and the time of measurement of the digital test data, and the data-processing means calculates, from the stored digital test data and time, the rate of change of the digital test data for comparison with further stored data in determining the concentration of the substance of interest.

16. An agglutination immunoassay method for quantitatively measuring the concentration of a biologically active substance of interest in a fluid sample, comprising:
   providing a fluid sample, which may contain the biologically active substance of interest;
   preparing uniformly sized particles formed of a copolymer of one monomer selected to inhibit their non-specific reaction to body fluids and another monomer selected to enhance their light-scattering properties, said particles being sensitized by functional groups at their surfaces to be capable of reacting with an antigen or antibody for the biologically active substance of interest;
   providing a reagent suspension comprising a buffered suspension of the sensitized particles with attached antigens or antibodies for the biologically active substance of interest;

mixing the reagent suspension with the fluid to be tested to provide an agglutination reaction;

passing a high-intensity beam of light through the fluid sample/reagent suspension mixture;

measuring the intensity of the light scattered by the mixture at an acute angle to the light beam to provide test data and storing the test data on the scattered light intensity; and comparing the stored test data with standard curve data to determine the concentration of the biologically active substance of interest in the fluid sample.

17. The method of claim 16 wherein the polymeric particles have a size of about 0.10 micron to about 0.35 micron, and wherein the high-intensity light comprises light at a wavelength of about 660 nanometers, and wherein the intensity of the light is measured at an acute angle of about 10° to about 20°.

18. The method of claim 16 wherein said polymeric particles have a size of about 0.10 micron to about 0.35 micron.

19. The method of claim 18 wherein said polymeric particles have a very uniform size of 0.18 micron ±0.01 micron.

20. The method of claim 16 wherein said fluid sample comprises blood serum and wherein a halogen-substituted carboxylic acid is added to said mixture for preventing spontaneous, non-specific agglutination from occurring in the mixture.

21. The method of claim 16 wherein said high-intensity beam of light comprises light at a wavelength of about 660 nanometers.

22. The method of claim 16 where the biologically active substance of interest is Theophylline and the step of providing a reagent suspension comprises providing a first reagent comprising at least a buffer and an anti-Theophylline antibody and a second reagent comprising a buffered suspension of sensitized particles with attached Theophylline antigens, and said first reagent and then said second reagent are mixed with said fluid sample and said concentration of Theophylline is determined in an indirect format.

23. The method of claim 22 wherein said antigen attached to the sensitized particles is Theophylline-8-hydroxypropylamine.

24. The method of claim 16 wherein said measuring step comprises measuring the intensity of the light scattered at an acute forward angle of about 10° to about 20° with a photodetector.

25. The method of claim 16 and further including the step of storing standard curve data representing the concentration of the biologically active substance of interest as a function of scattered light intensity and time, said comparing step comprising comparing the test data with the standard curve data to provide a quantitative measure of the concentration of the substance of interest in the fluid sample.

26. An agglutination immunoassay method for quantitatively measuring the concentration of a biologically active substance of interest in a fluid sample, comprising:

providing a fluid sample which may contain the biologically active substance of interest;

preparing uniformly sized, small particles formed of a copolymer of one monomer selected to inhibit their non-specific reaction to body fluids and another monomer selected to enhance their light-scattering properties, said particles being sensitized by functional groups at their surfaces and capable of reacting with the biologically active substance of interest;

providing a reagent suspension comprising a buffered suspension of the sensitized particles with attached biologically active substance of interest;

providing a reagent solution comprising a buffered solution containing antigens or antibodies for the biologically active substance of interest;

mixing the reagent suspension and the reagent solution with the fluid to be tested to provide an agglutination reaction;

passing a high-intensity beam of light through the fluid sample/reagent suspension mixture;

measuring the intensity of the light scattered by the mixture at an acute angle to the light beam to provide test data and storing the test data on the scattered light intensity; and comparing the stored test data with standard curve data to determine the concentration of the biologically active substance of interest in the fluid sample.

27. An agglutination immunoassay method, comprising:

providing one or more reagents, said one or more reagents comprising at least a suspension of uniformly sized, small particles composed of a copolymer of one monomer selected to provide a high index of refraction and another monomer selected to inhibit the particles' non-specific reaction to body serum, said particles having their surfaces sensitized to a biologically active substance of interest;

mixing with said one or more reagents a fluid to be tested for a biologically active substance of interest to create a reaction with said particles and to agglutinate said particles;

generating and directing a column of light at the agglutination reaction of the mixed one or more reagents and said fluid to be tested along a central light axis;

measuring the intensity of the light scattered by the particles resulting from said agglutination reaction at an acute angle offset from the central light axis; and determining from said measurement of the scattered light intensity the concentration of the biologically active substance of interest in the fluid.

28. The method of claim 27 wherein said uniformly sized, small particles are in the size range of about 0.10 to about 0.40 micron, said one monomer is an vinyl aromatic monomer and said other monomer is a vinyl acrylate ester monomer, and said acute angle is offset from the central light axis from about 10° to about 20°.

29. The method of claim 28 wherein said uniformly sized, small particles are in a size range of 0.18 micron ±0.1 micron and said acute angle is about 17°.

30. The method of claim 27 wherein the intensity of the light scattered by the agglutinated particles at an acute angle offset from the central axis is measured at a plurality of known times and the measured intensities and times are stored and compared with stored premeasured values of light intensities and times for the biologically active substance of interest at various concentrations to determine the concentration of the biologically active substance in said body serum.

31. The method of claim 30 wherein said plurality of stored values of intensity of the light scattered at a plurality of known times is used to calculate a rate of change of intensity and the rate of change of intensity is stored and compared with pre-measured values of rate of change of scattered light intensity for the biologically active substance of interest to determine the concentration of the biologically active substance in said body serum.

32. The method of claim 27, comprising providing a first reagent comprising at least a buffer and antibodies for the biologically active substance of interest, said suspension of uniformly sized small particles comprising a second reagent including buffered suspension of said particles with attached antigens for said antibodies.

33. The method of claim 32 wherein the biologically active substance of interest is Theophylline, the antibodies of the first reagent are mnonoclonal anti-Theophylline antibodies, the antigen of said second reagent are Theophylline-8- hydroxypropylamine, and the concentration of Theophylline is determined from the extent of inhibition of the agglutination reaction.

34. The apparatus of claim 1 wherein said light application and measurement system comprises a light source behind a first aperture plate and spaced a distance of about 1.320 inches from the first aperture plate, said first aperture plate forming an orifice with a diameter of about 0.200 inch, and said first aperture plate is spaced 0.790 inch from a collimating lens to provide a column of light having a diameter of about 0.200 inch, said collimating lens being spaced about 1.459 from the center portion of said fluid sample container.

35. The apparatus of claim 1 wherein said light application and measurement apparatus comprises a photodetector behind a light barrier plate forming an aperture having a diameter of about 0.152 inch, the aperture of said light barrier plate and said photodetector lying on an axis offset from the path of the column of light and at an acute angle of about 10° to about 20° with respect to the column of light.

36. The apparatus of claim 1 wherein the light application and measurement apparatus include a light-emitting diode capable of generating high-intensity light.

37. The apparatus of claim 36 wherein the light source is a high-intensity, light-emitting diode producing light at a wavelength of about 660 nanometers.

38. The apparatus of claim 36 wherein said light application and measurement apparatus further includes means to control the intensity of the light source, comprising a variable current supply for said light-emitting diode.

39. The apparatus of claim 38 wherein said processing and controlling apparatus is adapted to generate data on the intensity of the light from the light application and measurement apparatus, to store data on the calibrated output of the light application and measurement apparatus and to control said variable current supply to maintain the intensity of the light source to provide the calibrated output.

40. The apparatus of claim 35 wherein said apparatus includes a variable gain amplifier connected with the output of said photodetector and wherein said processing and controlling apparatus varies the gain of the variable gain amplifier for different tests.

41. The apparatus of claim 1 wherein said processing and controlling apparatus comprises:
an analog-to-digital converter for the errant-free output of the light application and measurement apparatus to generate digital information on the intensity of the scattered light;
a central processing unit connected with the analog-to-digital converter to receive the digital information on the scattered light intensity and to operate the apparatus;
a random access memory with sufficient addressable information storage capacity to store data on the scattered light intensities associated with a plurality of concentrations of a biologically active substance of interest and to store a plurality of digital data and time data resulting from the operation of the light application and measurement apparatus, an electrically programmable read-only memory with sufficient memory to store a program to operate the apparatus and to store and retrieve information from the random access memory and determine the concentration of biologically active substances of interest from data stored therein and resulting from operation of the apparatus; and
at least one information input device and one information output device.

42. The apparatus of claim 1 wherein said processing and controlling apparatus includes a replaceable test memory adapted for insertion and removal from the apparatus with sufficient memory to store a test program and standard curve data on one or more substances of interest.

43. The apparatus of claim 1 wherein said fluid sample container comprises a substantially parallel-sided, transparent sample container.

44. The apparatus of claim 41 further comprising an analog multiplexer interconnecting the light application and measurement apparatus and the analog-to-digital converter to provide the central-processing unit with a plurality of inputs from the light application and measurement apparatus.

45. The method of claim 28 wherein light is generated by a light-emitting diode with a wavelength of about 660 nanometers.

46. The method of claim 27 wherein said fluid sample comprises blood serum and wherein a halogen-substituted carboxylic acid is added to said one ore more reagents for preventing spontaneous, non-specific agglutination from occurring in the mixture.

47. The apparatus of claim 1 wherein said high-intensity beam of light comprises light at a wavelength of about 660 nanometers and wherein said measuring step comprises measuring the intensity of the light scattered at an acute forward angle of about 10° to about 20° with a photodetector.

48. The apparatus of claim 47 wherein said acute angle is about 17°.

49. A quantitative immunoassay method for determining the concentration of Theophylline in a fluid sample by an agglutination reaction, comprising:
providing a first reagent comprising at least a buffer and an anti-Theophylline antibody;
providing a second reagent comprising a buffered suspension of uniformly sized small particles, said particles being composed of a copolymer of one monomer selected to provide a high index of refraction and the other monomer selected to inhibit the particles' non-specific reaction to the serum or the fluid sample and having their surfaces adapted for attachment of Theophylline antigens;
mixing said first and second reagents and said fluid sample;

generating and directing a column of light at the mixture of the fluid sample and the first and second reagents;

measuring the intensity of the light scattered by the particles resulting from the agglutination reaction at an acute angle offset from the axis of the column of light; and determining from said measurement of the scattered light intensity the concentration of Theophylline in the fluid sample.

50. The method of claim 49 wherein said antibodies of the first reagent are monoclonal anti-Theophylline antibodies and said antigens of the second reagent are Theophylline-8-hydroxypropylamine.

51. The method of claim 49 wherein said uniformly sized, small particles are in the size range of about 0.10 to about 0.40 micron, said one monomer is an vinyl aromatic monomer and said other monomer is a vinyl acrylate ester monomer, and said acute angle is offset from the central light axis from about 10° to about 20°.

52. The method of claim 49 wherein said uniformly sized, small particles are in a size range of 0.18 micron ±0.1 micron and said acute angle is about 17°.

53. The method of claim 49 wherein the intensity of the light scattered by the agglutinated particles at an acute angle offset from the central axis is measured at a plurality of known times and the measured intensities and times are stored and compared with stored pre-measured values of light intensities and times for Theophylline at various concentrations to determine the concentration of Theophylline in said fluid sample.

54. The method of claim 49 wherein said plurality of stored values of intensity of the light scattered at a plurality of known times is used to calculate a rate of change of light intensity and the rate of change of light intensity is stored and compared with pre-measured values of rate of change of scattered light intensity for Theophylline to determine the concentration of Theophylline in said fluid sample.

55. The method of claim 54 wherein the maximum rate of change of intensity is calculated and compared with the pre-measured maximum rate of change of light intensity to determine the concentration of Theophylline in said fluid sample.

* * * * *

UNITED STATES PATENT AND TRADEMARK OFFICE
CERTIFICATE OF CORRECTION

PATENT NO. : 5,100,805   Sheet 1 of 3
DATED : March 31, 1992
INVENTOR(S) : Garth E. Ziege, et al.

It is certified that error appears in the above-identified patent and that said Letters Patent is hereby corrected as shown below:

In col. 1, line 29, delete "antibodyantigen" and insert therefor --antibody-antigen--.

In col. 7, line 58, after any delete "," (comma).

In col. 8, line 34, delete "include" and insert therefor --includes--.

In col. 8, line 56, delete "8" and insert therefor --$\theta$--.

In col. 18, line 15, delete "R'" and insert therefor --R--.

In col. 23, line 28, before "fluid" insert --a--.

In col. 23, line 30, delete "uniformity mixed" and insert therefor --uniformly sized--.

In col. 27, line 18, delete "mnonoclonal" and insert therefor --monoclonal--.

In col. 27, line 31, after 1.459 insert --inches--.

In col. 27, line 34, delete "apparatus" and insert therefor --system--.

UNITED STATES PATENT AND TRADEMARK OFFICE
CERTIFICATE OF CORRECTION

PATENT NO. : 5,100,805   Sheet 2 of 3
DATED : March 31, 1992
INVENTOR(S) : Garth E. Ziege, et al.

It is certified that error appears in the above-identified patent and that said Letters Patent is hereby corrected as shown below:

In col. 27, line 42, delete "apparatus" and insert therefor --system--.

In col. 27, line 48, delete "apparatus" and insert therefor --system--.

In col. 27, line 53, delete "apparatus" and insert therefor --system--.

In col. 27, line 55, delete "apparatus" and insert therefor --system--.

In col. 27, lines 56 and 57, delete "apparatus" and insert therefor --system--.

Column 27, line 60, delete "apparatus" (2nd occurrence) and insert therefor --system--.

In col. 27, line 63, delete "apparatus" and insert therefor --system--.

In col. 27, line 66, delete "apparatus" and insert therefor --system--.

In col. 27, line 68 and col. 28, line 1, delete "apparatus" and insert therefor --system--.

UNITED STATES PATENT AND TRADEMARK OFFICE
CERTIFICATE OF CORRECTION

PATENT NO. : 5,100,805
DATED : March 31, 1992
INVENTOR(S) : Garth E. Ziege, et al.

It is certified that error appears in the above-identified patent and that said Letters Patent is hereby corrected as shown below:

In col. 28, line 13, delete "apparatus" and insert therefor --system--.

In col. 28, line 24, delete "apparatus" and insert therefor --system--.

In col. 28, line 34, delete "apparatus" and insert therefor --system--.

In col. 28, line 37, delete "apparatus" and insert therefor --system--.

Signed and Sealed this

Twenty-second Day of June, 1993

Attest:

MICHAEL K. KIRK

*Attesting Officer*   *Acting Commissioner of Patents and Trademarks*